(12) United States Patent
Gamache et al.

(10) Patent No.: US 7,503,203 B2
(45) Date of Patent: Mar. 17, 2009

(54) ROTARY VALVE AND ANALYTICAL CHROMATOGRAPHIC SYSTEM USING THE SAME

(75) Inventors: Yves Gamache, Adstock (CA); André Fortier, Adstock (CA)

(73) Assignee: Mecanique Analytique Inc., Thetford-Mines, Quebec (CA)

( * ) Notice: Subject to any disclaimer, the term of this patent is extended or adjusted under 35 U.S.C. 154(b) by 810 days.

(21) Appl. No.: 10/957,560

(22) Filed: Oct. 1, 2004

(65) Prior Publication Data

US 2006/0042686 A1 Mar. 2, 2006

Related U.S. Application Data

(63) Continuation of application No. PCT/CA2004/001560, filed on Aug. 25, 2004.

(51) Int. Cl.
G01N 30/04 (2006.01)
(52) U.S. Cl. .................... 73/23.42; 137/51; 137/55; 137/625.46
(58) Field of Classification Search ............ 137/625.46; 73/863.73, 863.72
See application file for complete search history.

(56) References Cited

U.S. PATENT DOCUMENTS

| | | | |
|---|---|---|---|
| 2,519,574 A | 8/1950 | Holl | |
| 3,203,249 A | 8/1965 | Jentzsch et al. | |
| 3,223,123 A | 12/1965 | Young | |
| 3,297,053 A | 1/1967 | McKinney | |
| 4,068,528 A | 1/1978 | Gundelfinger | |
| 4,182,184 A | 1/1980 | Bakalyar et al. | |
| 4,222,412 A | 9/1980 | Carle | |
| 4,242,909 A | 1/1981 | Gundelfinger | |
| 4,243,071 A | 1/1981 | Shackelford | |
| 4,393,726 A | 7/1983 | Tamm et al. | |
| 4,476,731 A | 10/1984 | Charney et al. | |
| 4,506,558 A | 3/1985 | Bakalyar | |
| 4,577,515 A | 3/1986 | Someya et al. | |
| 4,702,889 A * | 10/1987 | Cabrera et al. | 422/103 |
| 5,193,581 A | 3/1993 | Shiroto et al. | |
| 5,207,109 A * | 5/1993 | Olsen | 73/863.73 |
| 5,803,117 A | 9/1998 | Olsen et al. | |
| 6,012,488 A | 1/2000 | Nichols | |
| 6,067,864 A | 5/2000 | Peterson | |
| 6,155,123 A | 12/2000 | Bakalyar | |
| 6,316,759 B2 * | 11/2001 | Gaisford et al. | 219/748 |
| 6,453,946 B2 | 9/2002 | Nichols et al. | |
| 6,672,336 B2 | 1/2004 | Nichols | |
| 6,997,213 B1 * | 2/2006 | Towler et al. | 137/625.46 |
| 7,096,886 B2 * | 8/2006 | Hofmann | 137/625.46 |
| 2004/0112444 A1 | 6/2004 | Biospin | |

* cited by examiner

*Primary Examiner*—Hezron Williams
*Assistant Examiner*—Mark Shabman
(74) *Attorney, Agent, or Firm*—Darby & Darby PC

(57) ABSTRACT

There is provided a rotary valve for fluid analytical systems. The present valve provides improved characteristics such as an extended lifetime. The valve can fulfil different fluid analytical functions and can be a multi-ports and/or multi-positions valve. The valve is provided with extra recesses in the rotor and extra ports in the stator. These recesses allow to cancel the effect of any possible leaks by evacuating them. Such a valve then prevents cross-port leaks and can advantageously be used in highly critical applications. Moreover, the present valve can be used in an analytical system which is advantageously self-diagnostic.

26 Claims, 21 Drawing Sheets

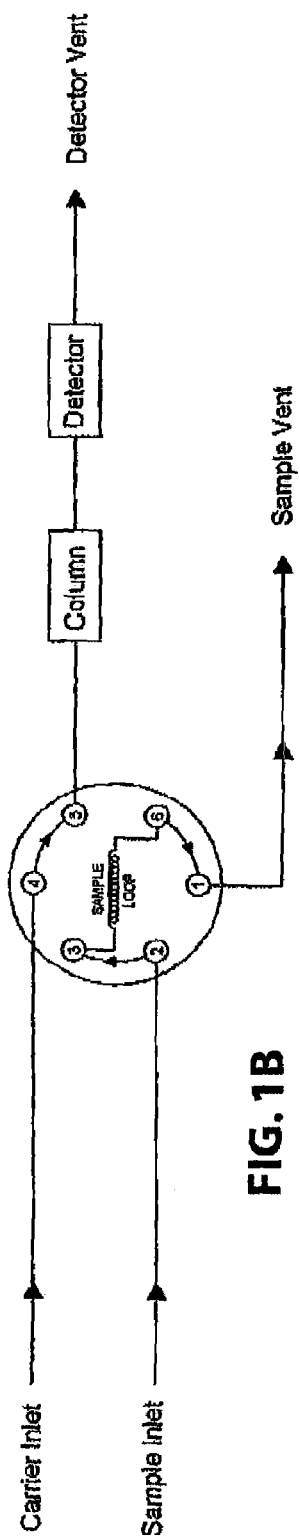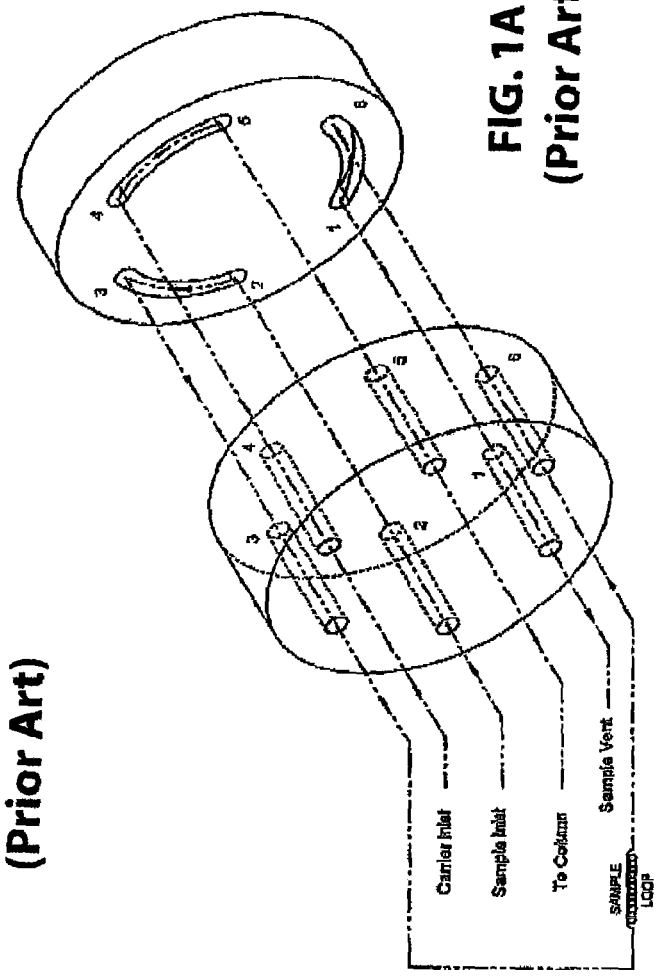
FIG. 1B (Prior Art)
FIG. 1A (Prior Art)

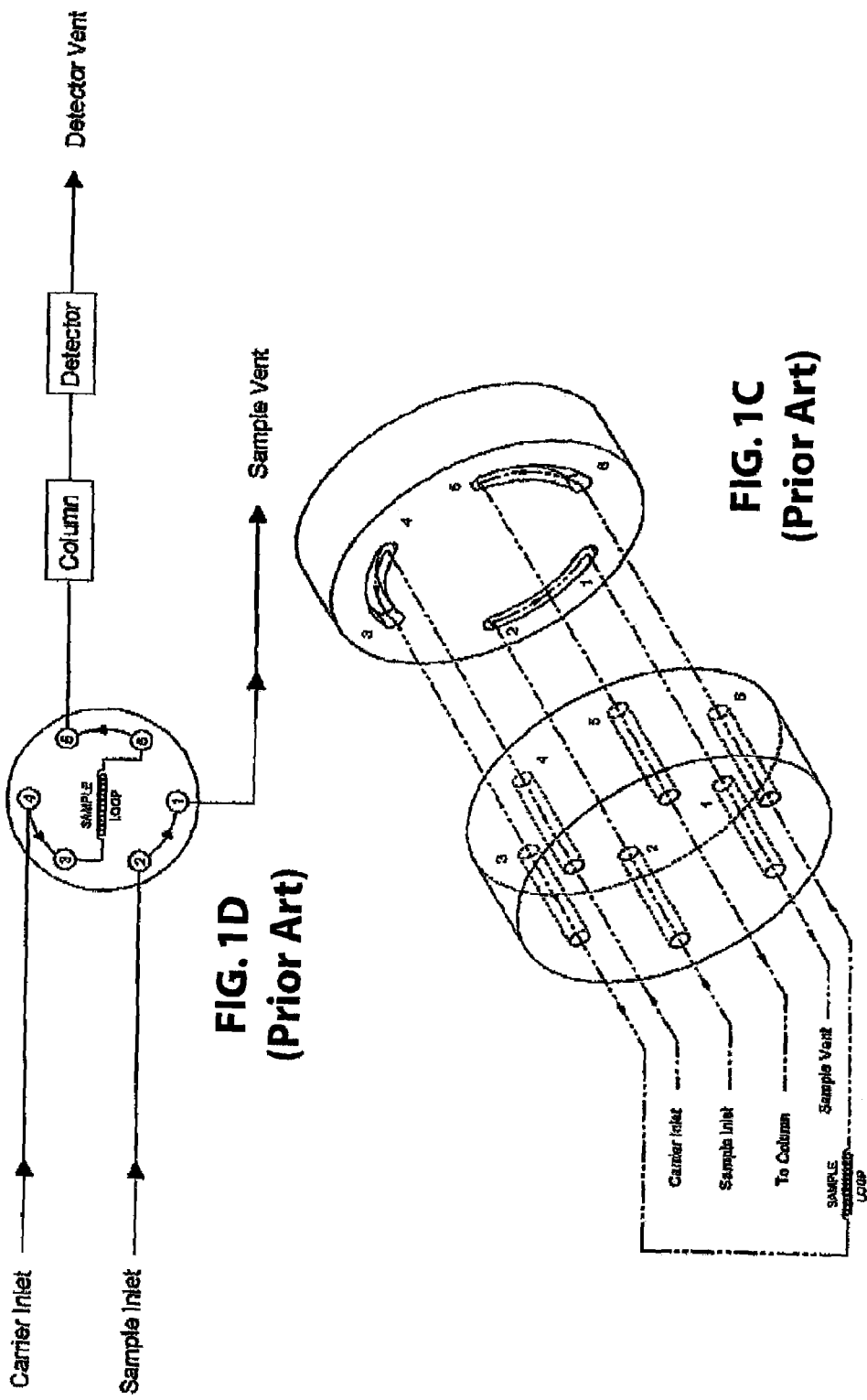

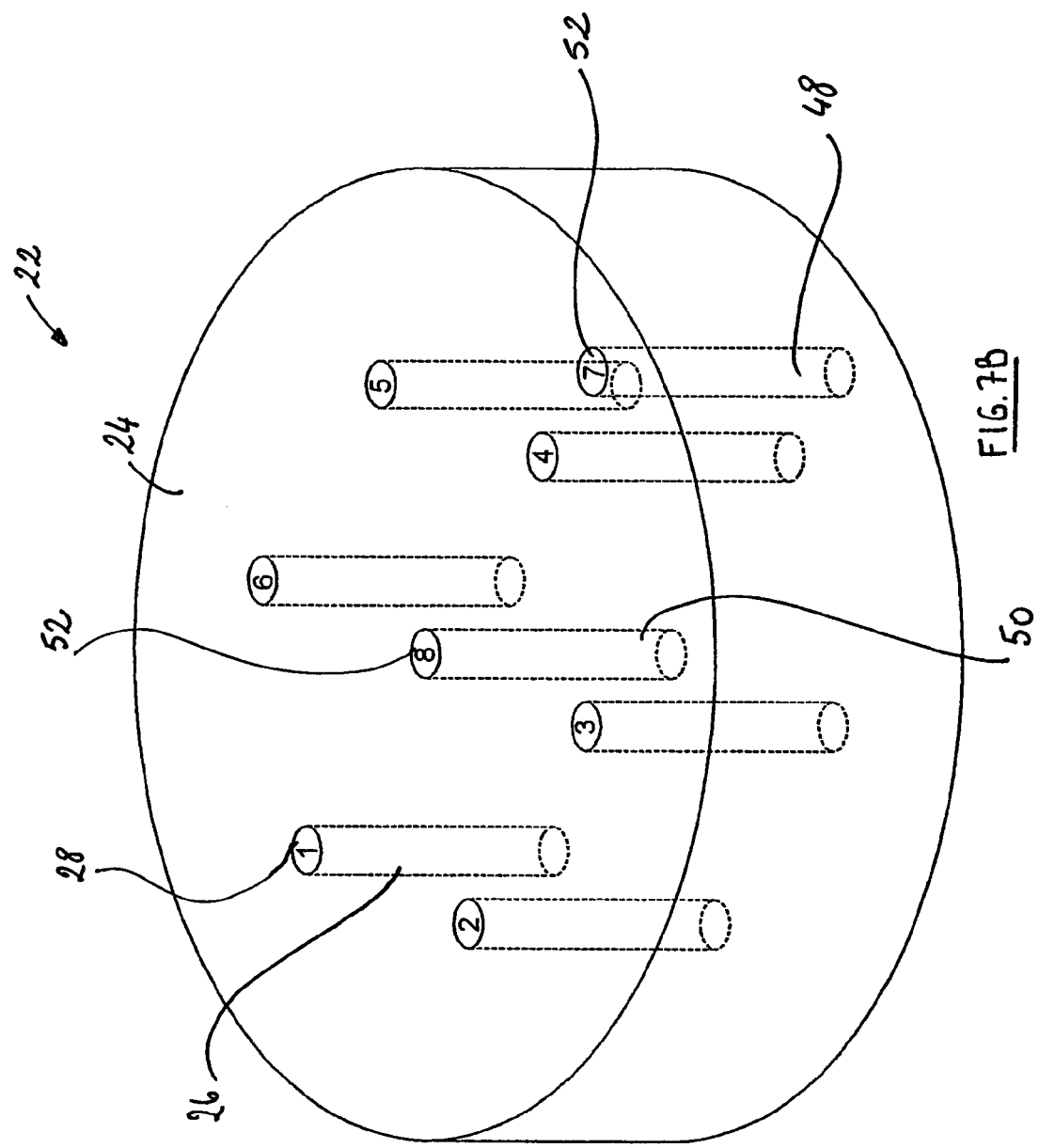

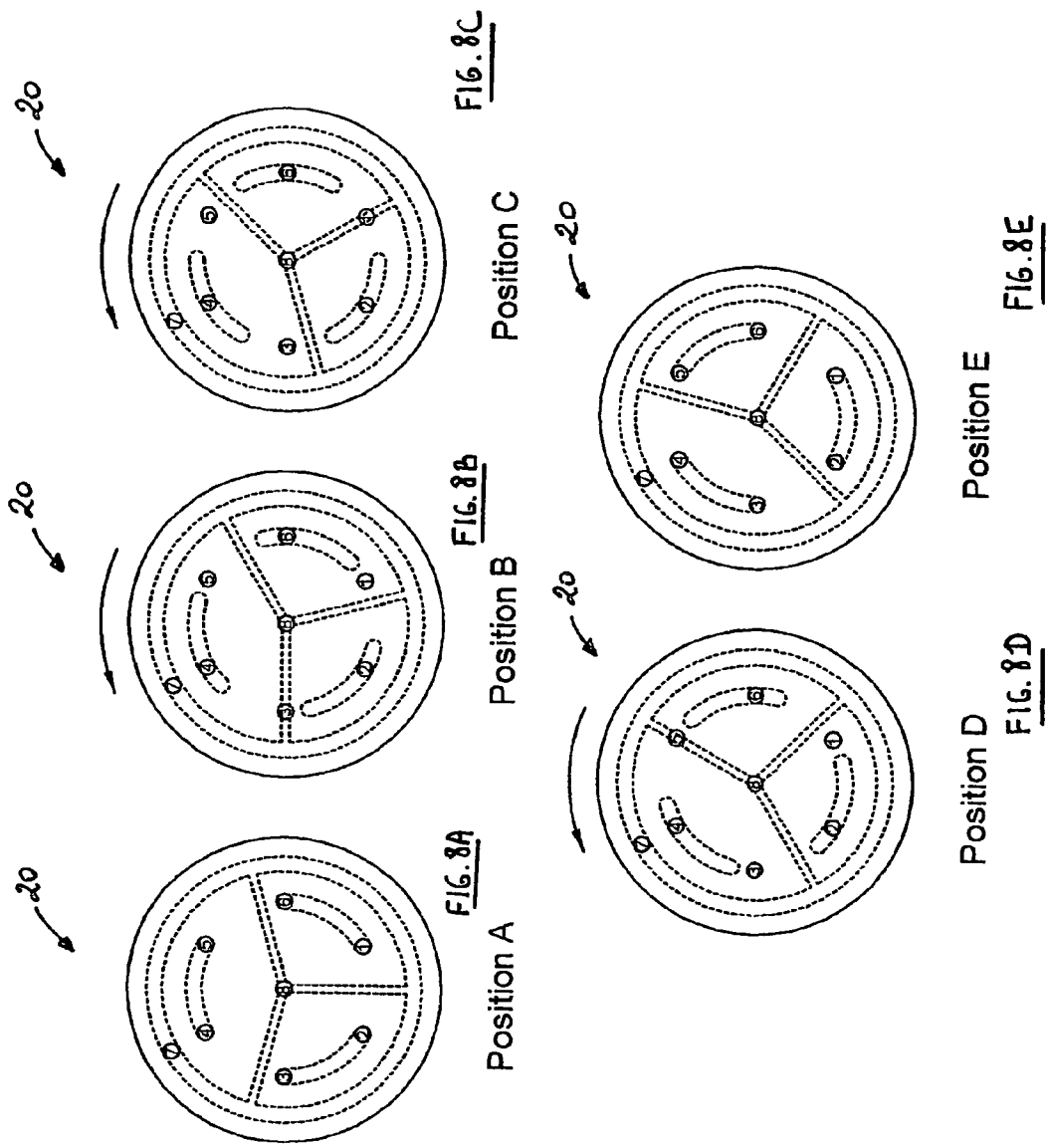

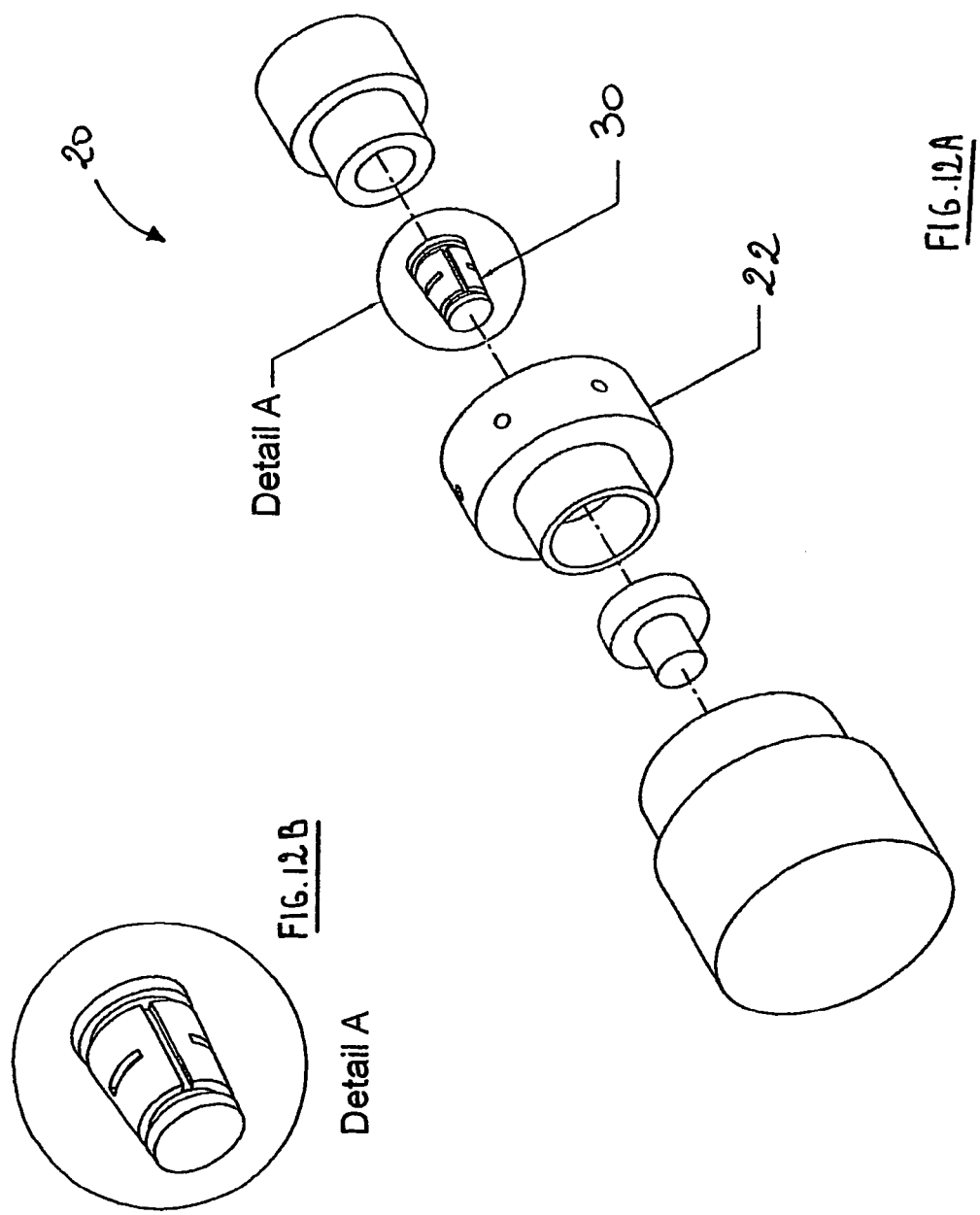

ROTARY VALVE AND ANALYTICAL CHROMATOGRAPHIC SYSTEM USING THE SAME

FIELD OF THE INVENTION

The present invention generally relates to a rotary valve for fluid analytical systems, and more particularly concerns a rotary valve having improved characteristics. The present invention also concerns an analytical chromatographic system using such a rotary valve.

BACKGROUND OF THE INVENTION

In various analytical methods, i.e. chromatography, online measurement and others, many scientific instruments need fluid controlling device. Most of the time, this is achieved by using different types of fluid flow path switching valves. As non-limitative examples, the function of these valves could be for sample injection, sample stream selection, fluid redirection, fraction collection, solvent selection, separation column selection or combination and other fluid switching flow paths required to realize a particular analytical method.

In these systems, the fluid pressure range could be from vacuum to value in the neighbourhood of 10,000 psig. The fluid phase could be gas or liquid. For the accuracy, precision and repeatability of the analytical method in the determination of impurities to be identified and quantified, it is of prime importance that the valves used in such method fulfil the most stringent parameters like inboard contamination, cross-port leak, leak from the inside to the outside of the system, dead volume, inertness and adsorption. In some cases the valve should be able to operate at high temperature, like 400° C., without the loss of its characteristic.

Several of these analytical methods are used in scientific instruments dedicated to be embedded in industrial process control equipment. In such applications, the analytical system must operate continuously and without human intervention. To realize an analytical system and method that meets these criteria, valves must be able to work appropriately for a long period of time, preferably two years or more, before any maintenance needs to be done on them.

Hereinbelow, several analytical method examples will be explained to help the reader understand how valve characteristic could affect overall system performance. They are not exclusive and there are dozens of valve and column combinations based on analytical methods used for any particular application. However, in all possible methods, the valve characteristic is a key parameter for system performance.

Referring to FIGS. 1A to 1D, there is shown a prior art six-ports valve used in a gas chromatography method. This is the simplest chromatography application. The sample to be analyzed flows into the sample loop. The separation column and the detector are swept by a very pure carrier gas, as illustrated in FIGS. 1A and 1B. When the valve's rotor is rotated on stator surface, the new groove alignment results in a new fluid flow path, as shown in FIGS. 1C and 1D. This position is commonly named the "sample injection" position. In this position, the sample loop content is carried to the separation column and then to the detector by the carrier gas. The various impurities are separated on the separation column and independently generate a signal from the detector having the shape of a Gaussian peak. The surface of this peak is integrated to calculate its area, by the supporting hardware and software, commonly know as an "Integrator". The computed area is then scaled to report the quantity of impurities in some engineering unit. The valve is then restored to the sampling position shown in FIGS. 1A and 1B to start a new analyzing cycle.

FIGS. 2A to 2C show another common configuration using two six-ports valves and two separation columns. This configuration is often used when the sample matrix, i.e. sample background, is different from the carrier gas. In this case, if the sample background reaches the detector, a huge peak will result, masking some of the impurities of interest, and some types of detectors could be damaged by overloading. To avoid this, most of the sample background is first "heartcuted" or vented outside the system by the first column. This is achieved by rotating the rotor of valve V1 in the sample injection position to inject a sample, as illustrated in FIG. 2B. Then, at the appropriate time, valve V2's rotor is rotated to direct the effluent coming out of the first column outside the system, as illustrated in FIG. 2C. The valve V2 is then restored to its original position when most parts of sample background have been vented and before impurities of interest come of the first column. Then, in the second column, which is an analytical column, the impurities will be separated and sequentially introduced in the detector. No detector overload will occur since little or no sample background is present.

There are many two or multi-positions rotary valves on the market, all of them having a stator and a rotor, these two parts generally consisting of a planar surface. Most of the time, one planar surface is harder than the other one. For the sake of the discussion, see FIGS. 1A to 1D, which show a typical sample injection rotary valve used in chromatography. The fluid flow path is changed by turning the rotor on stator surface. FIGS. 1A and 1B show the valve in sampling position while FIGS. 1C and 1D show the valve in sample injection position. The sealing action is provided by strongly pressing the rotor on the stator surface. Most of the time, the rotor is made of a softer material than the one of the stator. The stator is generally polished in order to get a flat surface and minimum roughness. Different types of materials have been used for stator and rotor, i.e. metal, ceramic and various polymers. When fluid is liquid, leaks are much lower than when the fluid is gaseous, even for the same operating pressure. Molecule sizes are much bigger and their shapes much more complex for liquids than gases.

In chromatograph applications using liquid media, operating pressures are quite high, sometimes up to 10,000 psig. Such high operating pressure requires a good sealing surface to minimize leaks.

For gaseous applications, the operating pressure is much lower and most of the time below 300 psig and typically 100 to 150 psig. However, when the carrier or sample is $H_2$ or He, a good sealing is extremely difficult to achieve.

The diameter of a He molecule is about 0.26 nm. The smallest scratch on the stator or rotor surface resulting from surface finish imperfection will cause leaks from port to port. The surface finish can be seen as a network of grooves with a random distribution. This makes it difficult to get good sealing for long periods of time. Nowadays, analytical methods and systems in which such valve is used are more efficient. This means that the total analytical cycle time has been cut in some cases by a factor of ten. The valves are therefore actuated much more often, their lifetime is then reduced and frequent maintenance is required. As reported in U.S. Pat. No. 6,453,946, such maintenance was previously required every six months, but it may now be required every week. Equipment downtime is undesirable.

In laboratory environment, frequent downtime could be at the limit acceptable. In this environment, there are always technicians to take care of analytical equipment and to reconfigure them for a new analytical method. However, for process chromatograph, frequent downtime is a serious problem. Process gas chromatograph must operate continuously as stand-alone unit. The analytical results of process gas chromatograph are the inputs of complex process control loop. When a valve slowly begins to leak, the analytical results become unstable and inaccurate. This may have a dramatic effect on a particular manufacturing process.

In rotary valves used in prior art, there is a fixed and a movable part, commonly known as stator and rotor. An example of such assembly is shown in FIGS. 3A to 3D. Generally, the rotor has some channels therein to allow for various gas connections of stator ports. The change in fluid flow path is done by turning the rotor on the stator surface. The rotation movement changes the rotor channels position seen by stator's ports. Thus, different flow paths can be achieved by changing channels configuration in the rotor and the number of ports in the stator.

Referring now to FIGS. 4A to 4D, there is shown two configurations for 10 and 12-ports valves respectively. FIGS. 5A and 5B show a configuration for sample stream selection. These configurations are not limitative or exclusive and many others could be done.

There are several embodiments of rotary valve systems known in the art. Some of them are designed simply for sample loop injection, others for syringe sample loading and others for multi-positions flow path switching. The port numbers vary from 4 to typically 12. For sample stream selection, the number of ports could be higher. All of them suffer from fast wearing caused by particle contamination, or simply by the friction between the various planar surfaces. There are no means to prevent or delay cross-port flow contamination over the time. Such rotary valve systems are disclosed in the following U.S. Pat. Nos. 3,203,249; 3,223,123; 3,297,053; 4,068,528; 4,182,184; 4,242,909; 4,243,071; 4,393,726; 4,476,731; 4,506,558; 4,577,515; 5,207,109; 5,803,117; 6,012,488; 6,155,123 and 6,672,336. All of them rely on flat surface sealing that lasts, at the best, around 9 months.

In the art, there are some valves that have a conical shape, as shown in FIGS. 6A and 6B, or a spherical shape, but they all suffer from the same problems. The conical valve concept shown in FIGS. 6A and 6B is largely used in most laboratory chromatographs. This valve is manufactured by the Valco Company and U.S. Pat. No. 4,222,412 illustrates such a valve.

An early attempt to fix one of the pre-cited problem, i.e. in this case, inboard or outboard leak, is shown in U.S. Pat. No. 2,519,574. Even if the described rotary 4-way valve is not specifically designed to be used in analytical systems, the concept shown could nevertheless be applied to it. The circular fluid O-ring type seal shown between the two planar surfaces will avoid leaking from the interior of the valve to the exterior of it and prevent inboard contamination too. However, this type of seal requires frequent replacement. Sealing effect relies on constant pressure applied by both planar surfaces on the seal, particle contamination causes seal wearing and leaks occur. The material used (generally elastomer but others are possible) could also desorb or adsorb some sample molecules when the pressure and/or temperature are changed. Furthermore, no means are provided to avoid cross-port leaks when the surface becomes scratched by the fluid's particle or by particles coming from the seal wearing.

Also known in the art, there is U.S. Pat. No. 5,193,581, which describes a way to eliminate the contamination of a selected sample by the unselected sample streams. There is an evacuation groove in the rotor that will carry away the leak coming from unselected channels, however there are serious drawbacks. This method does not fix the problem of cross-port leak between unselected ports. This is very important if various samples are reactive and non compatible. There is also a dead volume in the rotor. There is also an O-ring between the rotor and valve housing acting as a seal, so out-gassing could occur and O-ring wearing will cause leak.

Also known in the art, there is U.S. Pat. No. 6,067,864, which also describes a rotary sample selection valve that tries to eliminate the contamination of the selected sample by the unselected ones. The method uses a vacuum source to evacuate all the unselected channel through a common port. There is always a positive pressure differential between selected channels and the unselected evacuation volume. However, there is also a serious drawback since the system uses O-ring for sealing. So, out-gassing will occur as well as leaks because of wearing. Furthermore, all unselected sample streams must be compatible, since they are mixed together.

Also known in the art, there is U.S. Pat. No. 6,453,946, which describes a method to extend the valve's life. This method suggests the use of vespel as material for the rotor and stainless steel coated with tungsten carbide/carbon (WC/C). Even if this method helps to have a longer lifetime before leaks occur, it will not last two or three years. They report 200,000 cycles, however, valve actuated every two minutes in a process gas chromatography system will have more than 200,000 cycles after a year. Leaking will therefore occur and maintenance will be required.

Thus, a rotary valve overcoming the drawbacks of the existing ones while providing the long lifetime needed in process analytical equipment would be desirable.

SUMMARY OF THE INVENTION

An object of the present invention is to provide a rotary valve that satisfies the above-mentioned needs.

Accordingly, the present invention provides a rotary valve provided with a stator having a stator interface and a plurality of fluid open-ports, each of the ports having an opening lying at the stator interface. The rotary valve is also provided with a rotor coaxial to the stator and rotatable about an axis with respect to the stator between each of a plurality of rotor positions. The rotor has a rotor interface lying against the stator interface. The rotor is also provided with at least one fluid channel having an opening extending in the rotor interface for operatively interacting with the fluid open-ports of the stator. The rotary valve is also provided with a fluid circulation line comprising a looped recessed fluid circuit extending in the rotor interface. The looped fluid circuit has an outer annular recess and an inner recess, each extending in the rotor interface. The fluid circuit further has a plurality of separation recesses radially extending in the rotor interface. Each of the separation recesses is connected to each of the inner and outer recesses for defining a plurality of rotor interface portions isolated from each others. Each of the rotor interface portions encloses at the most one of the fluid channels. The fluid circulation line is also provided with a fluid inlet and a fluid outlet, each having an opening lying at the stator interface. Each of the inlet and outlet is in continuous fluid communication with a respective one of the inner and outer recesses for providing a continuous fluid flow in the looped recessed fluid circuit.

In a preferred embodiment of the present invention, each of the fluid channels extends in a respective one of the rotor interface portions. Each of the fluid channels is particularly shaped for connecting two adjacent ports when the rotor is in one of the rotor positions, thereby providing a fluid flow path between the two adjacent ports in said position. Preferably, the ports are circularly arranged in a port circle concentrical with the stator interface between the inner and outer recesses of the rotor and each of the fluid channels curvely extends in the rotor interface coincidentally with the circle.

In another preferred embodiment of the present invention, the inner recess has an annular portion defining a central rotor interface portion therein. The ports are particularly arranged so that at anyone of the rotor positions one of the ports is aligned with one of the rotor interface portions. The fluid channel has first and second openings extending in the rotor interface. The first opening extends in the central rotor interface portion and provides a continuous fluid communication with a corresponding port aligned therewith. The second opening extends in one of the remaining rotor interface portions and provides a fluid communication with a corresponding port aligned therewith for a given rotor position, thereby providing a fluid flow path between the two ports in simultaneous fluid communication with the first and second openings.

In a further preferred embodiment of the present invention, one of the ports is aligned with the central rotor interface portion. The remaining ports are arranged in pairs of first and second ports, each of the pairs being aligned with one of the rotor interface portions. The fluid channel has first and second openings extending in the rotor interface. The first opening extends in the central rotor interface portion and provides a continuous fluid communication with the corresponding port aligned therewith. The second opening extends in one of the remaining rotor interface portions and provides a fluid communication with one port of a corresponding pair aligned therewith for a given rotor position, thereby providing a fluid flow path between the two ports in simultaneous fluid communication with the first and second openings. The rotor is further provided with a plurality of recessed grooves. Each of the recessed grooves extends in a respective one of the remaining rotor interface portions for respectively connecting each port of a corresponding pair together in one of the rotor positions, thereby providing a vented fluid flow path between each port of the corresponding pair.

According to another aspect of the invention, there is provided an analytical chromatographic system provided with the rotary valve. The analytical chromatographic system is also provided with monitoring means operatively connected to the fluid outlet for monitoring a fluid passing therethrough.

Advantageously, the rotary valve of the present invention prevents cross-port leaks and allows to cancel the effect of any possible leaks by evacuating them. Furthermore, the sweeping action of the rotor's separation recesses and the corresponding flowing fluid advantageously eliminate the build up and the possibilities of particles trapping that will otherwise dramatically damage the rotor and stator surface. The sweeping fluid in the rotor's separation recesses advantageously provide a self cleaning action. The present rotary valve also presents an improved lifetime.

BRIEF DESCRIPTION OF THE DRAWINGS

These and other objects and advantages of the invention will become apparent upon reading the detailed description and upon referring to the drawings in which:

FIG. 1A (PRIOR ART) is an exploded perspective view of a conventional rotary valve in a sampling position known in the art.

FIG. 1B (PRIOR ART) is a schematic representation of a sample injection system using the rotary valve of FIG. 1A in the sampling position.

FIG. 1C (PRIOR ART) is an exploded perspective view of the rotary valve shown in FIG. 1A in a sample injection position.

FIG. 1D (PRIOR ART) is a schematic representation of the sample injection system shown in FIG. 1B in the sample injection position.

FIG. 7B is a perspective view of the stator of the rotary valve shown in FIG. 7A.

FIGS. 8A to 8E are front plan views of the rotary valve shown in FIG. 7A in different positions.

FIG. 12A is an exploded perspective view of another rotary valve, according to another preferred embodiment of the present invention.

FIG. 12B is an enlarged perspective view of the rotor of the rotary valve shown in FIG. 12A.

Figure 2A:
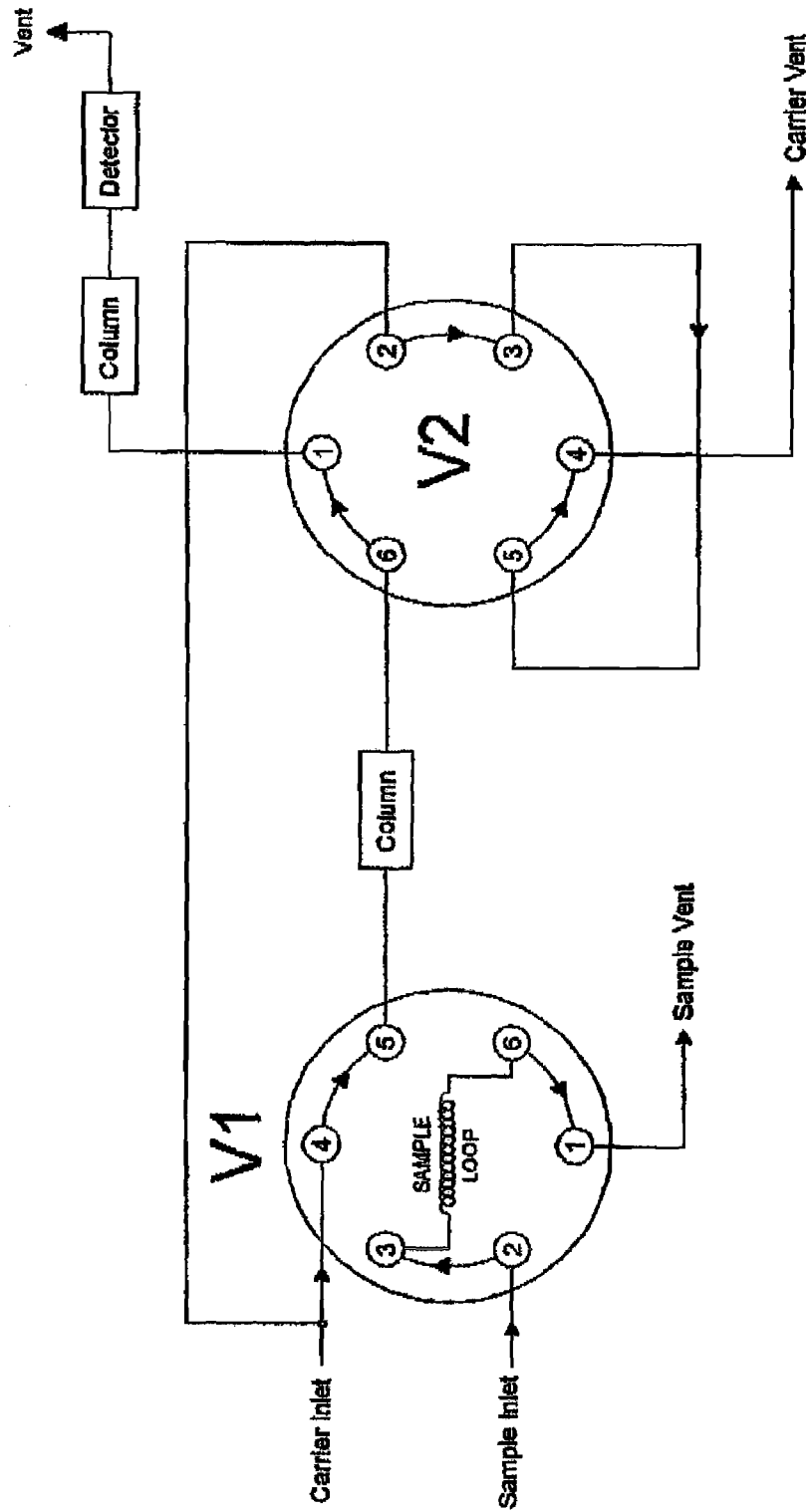
FIG. 2A (PRIOR ART) is a schematic representation of another sample injection system using the rotary valve of FIG. 1A, the system being in a sampling position.
Figure 2B:
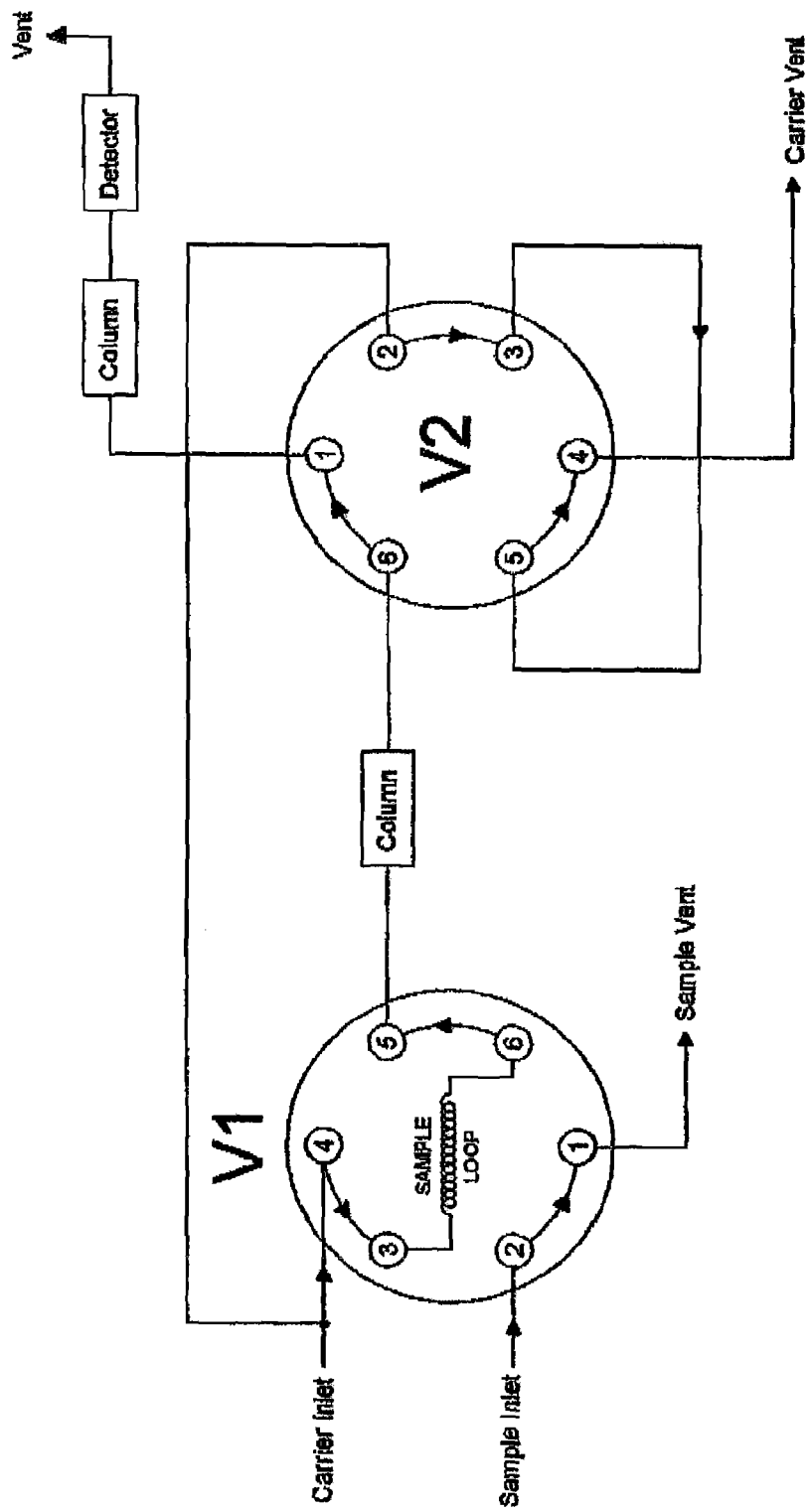
FIG. 2B (PRIOR ART) is a schematic representation of the sample injection system shown in FIG. 2A, the system being in a sample injection position.
Figure 2C:
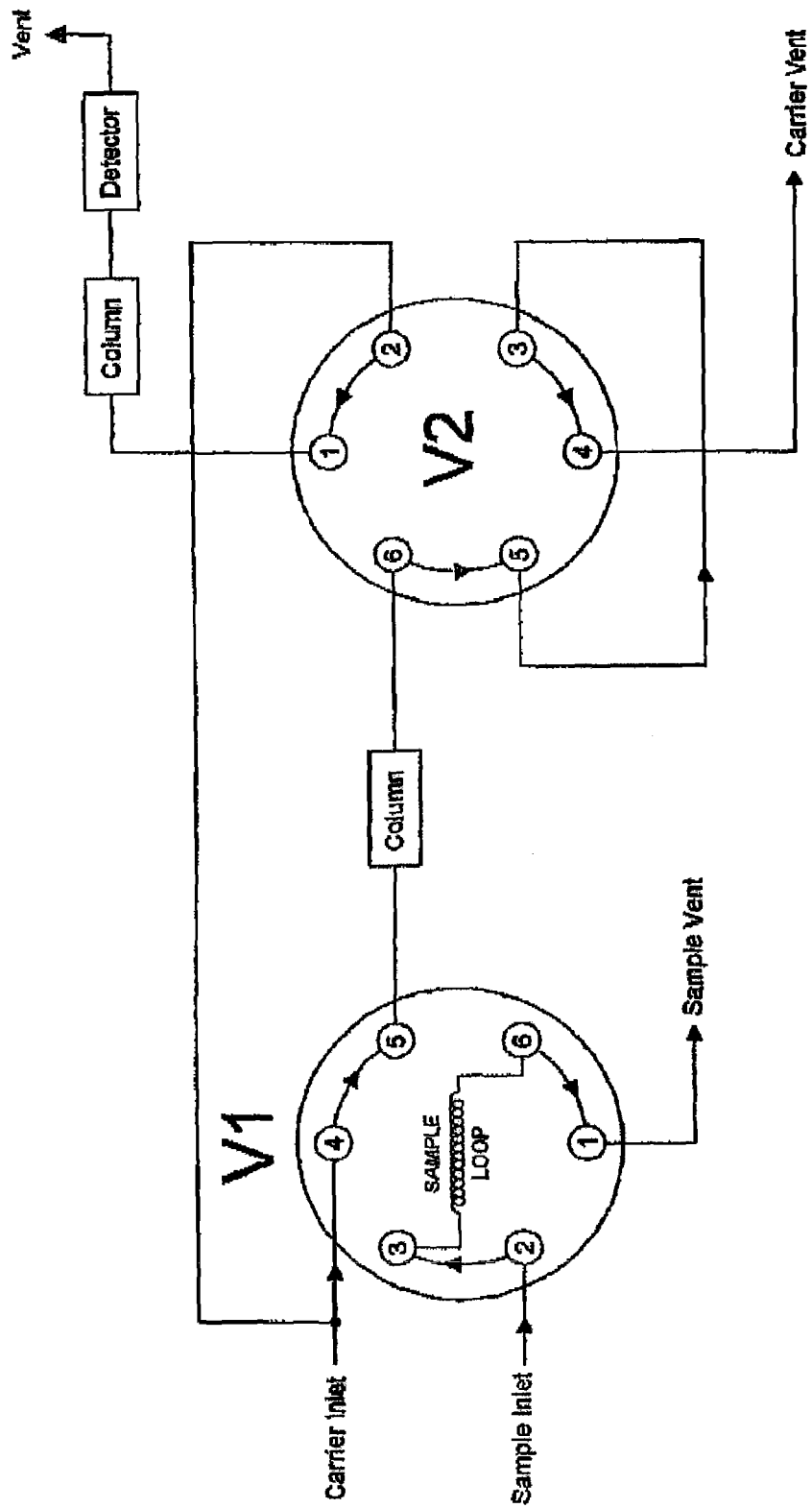
FIG. 2C (PRIOR ART) is a schematic representation of the sample injection system shown in FIG. 2A, the system being in a heart-cutting position.
Figure 3A:
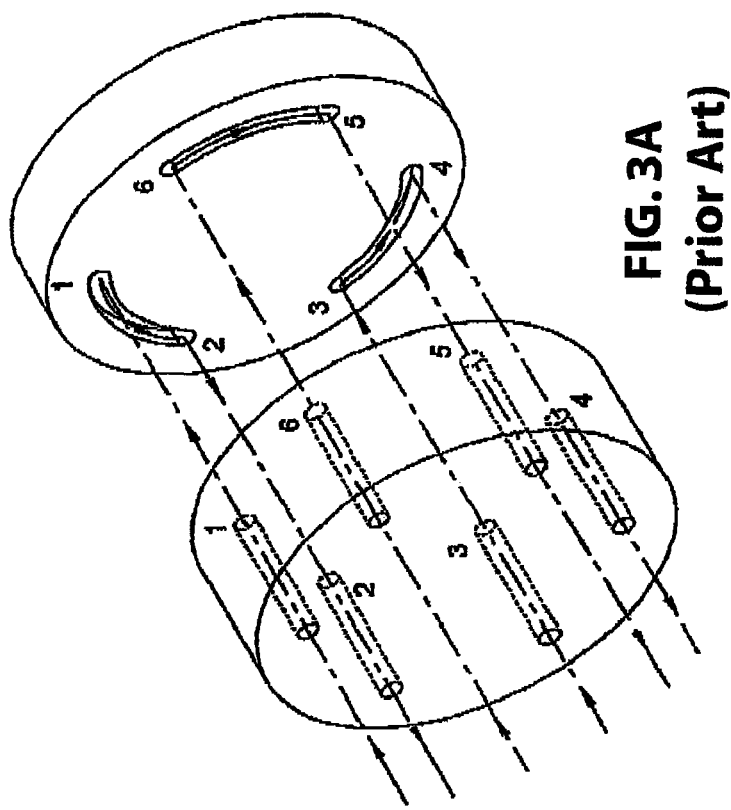
FIG. 3A (PRIOR ART) is an exploded perspective view of another rotary valve in a sampling position known in the art.
Figure 3B:
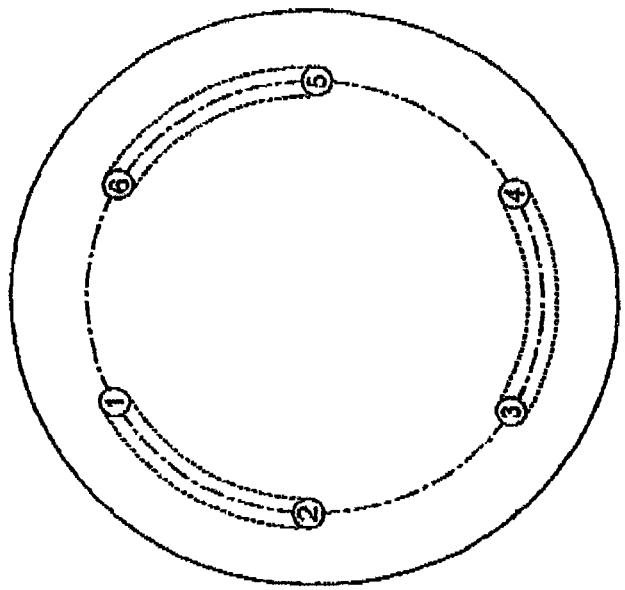
FIG. 3B (PRIOR ART) is a front plan view of the rotor of the rotary valve shown in FIG. 3A.
Figure 3C:
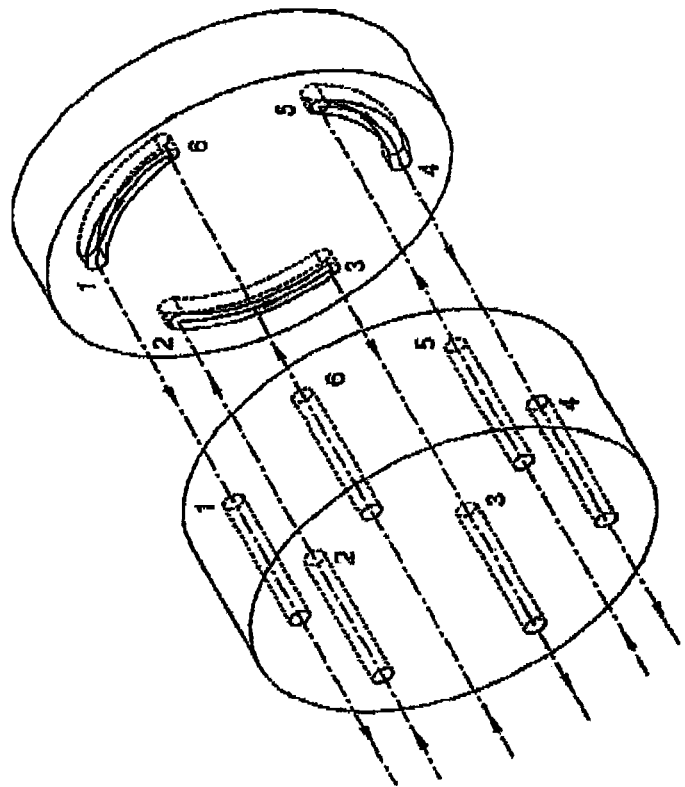
FIG. 3C (PRIOR ART) is an exploded perspective view of the rotary valve shown in FIG. 3A in a sample injection position.
Figure 3D:
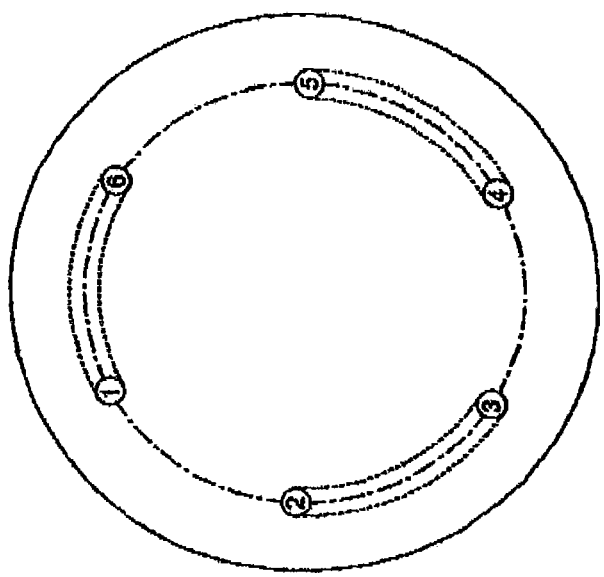
FIG. 3D (PRIOR ART) is a front plan view of the rotor of the rotary valve shown in FIG. 3C.
Figure 4A:
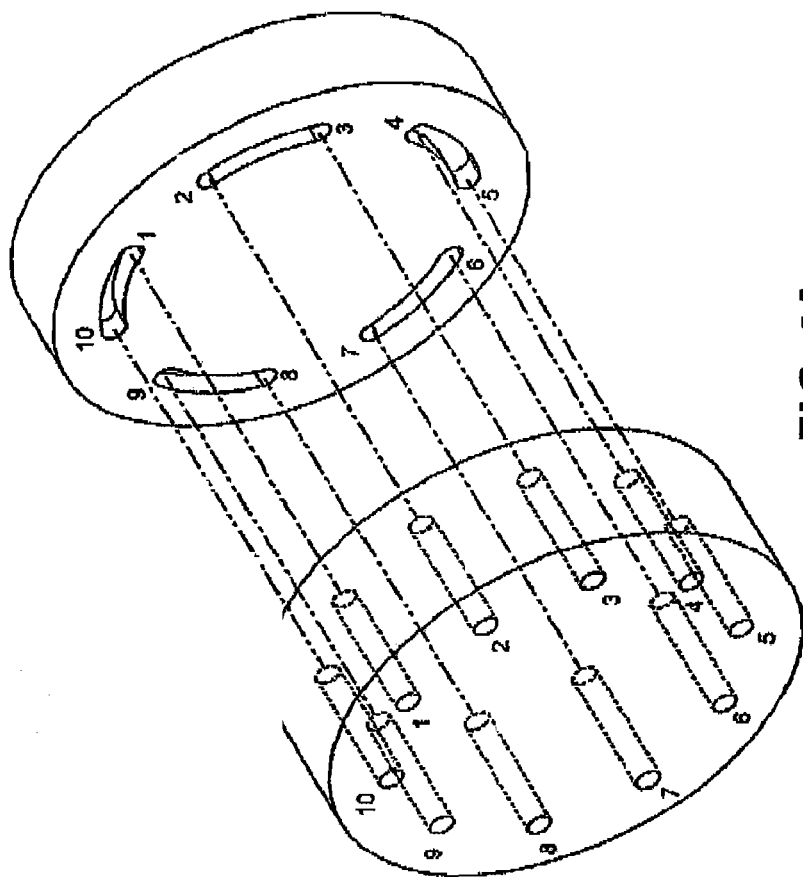
FIG. 4A (PRIOR ART) is an exploded perspective view of another rotary valve known in the art.
Figure 4B:
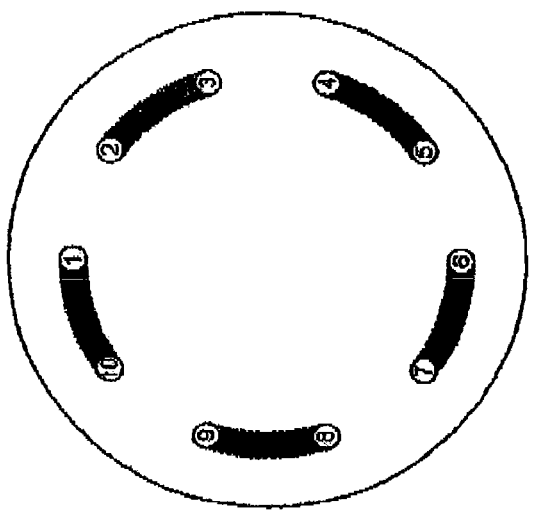
FIG. 4B (PRIOR ART) is a front plan view of the rotor of the rotary valve shown in FIG. 4A.
Figure 4C:
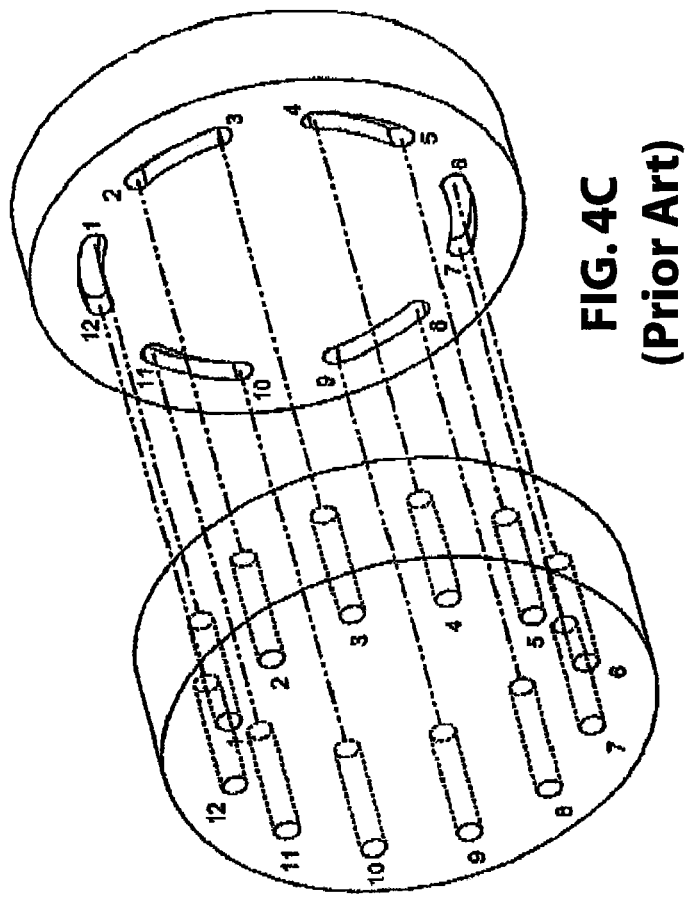
FIG. 4C (PRIOR ART) is an exploded perspective view of another rotary valve known in the art.
Figure 4D:
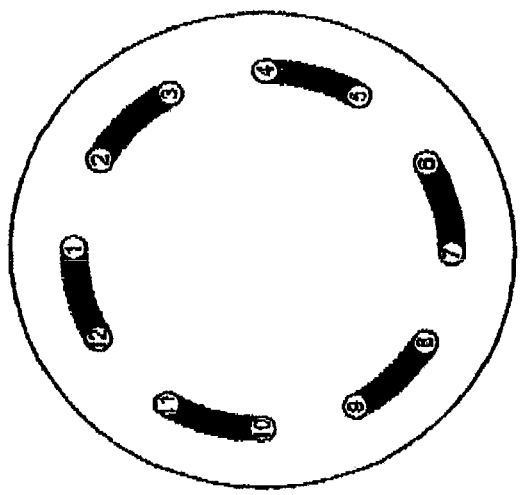
FIG. 4D (PRIOR ART) is a front plan view of the rotor of the rotary valve shown in FIG. 4C.
Figure 5A:
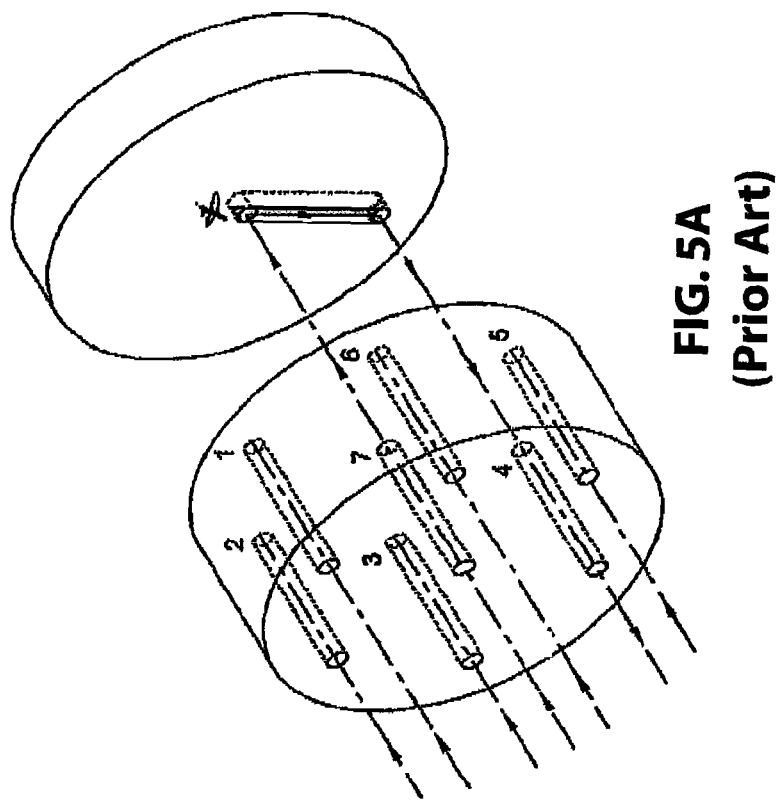
FIG. 5A (PRIOR ART) is an exploded perspective view of another rotary valve known in the art.
Figure 5B:
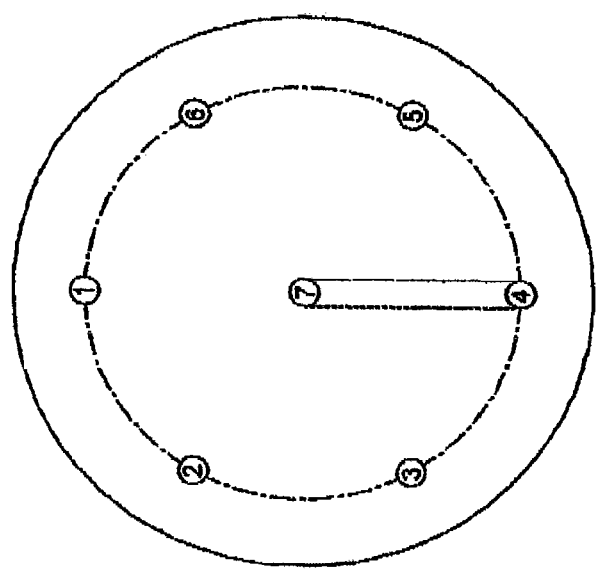
FIG. 5B (PRIOR ART) is a front plan view of the rotary valve shown in FIG. 5A.
Figures 6A, 6B:
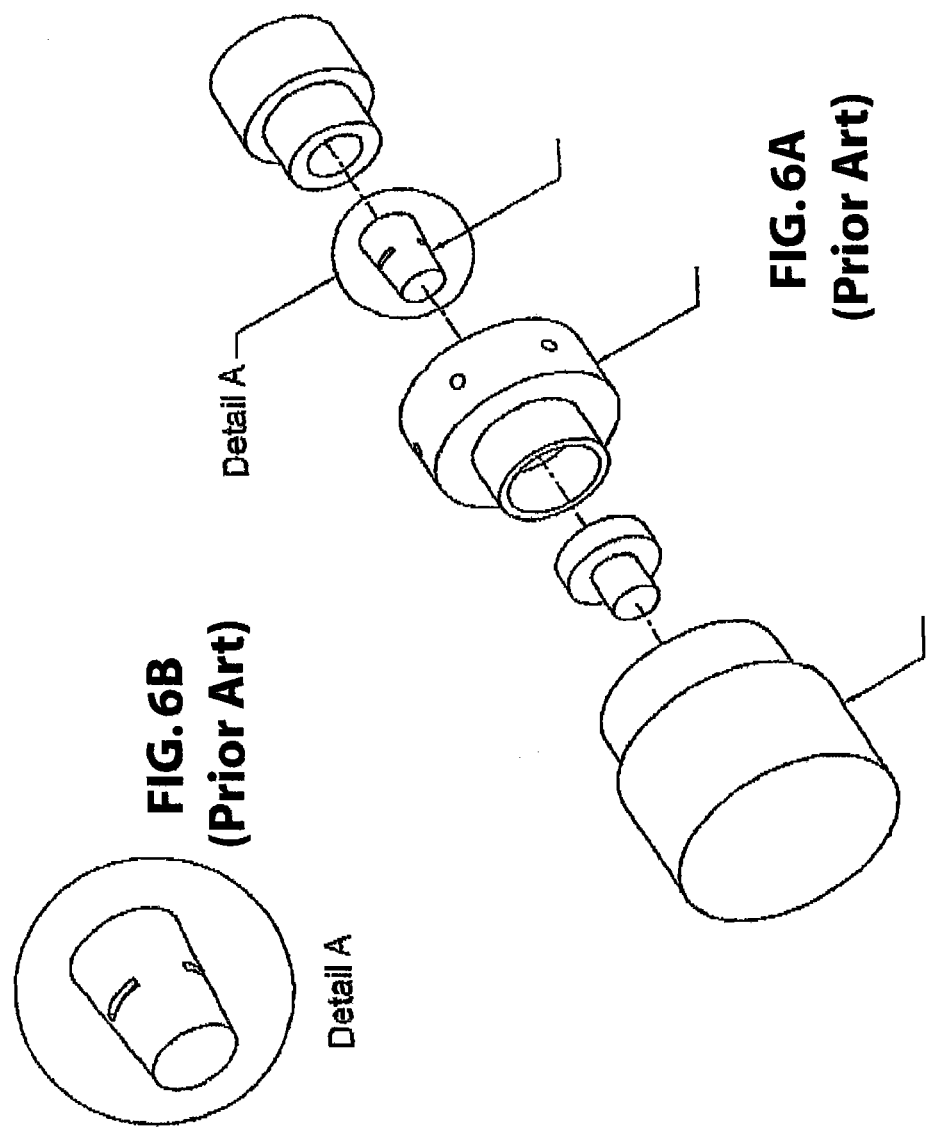
FIG. 6A (PRIOR ART) is an exploded perspective view of another rotary valve known in the art.
FIG. 6B (PRIOR ART) is an enlarged perspective view of the rotor of the rotary valve shown in FIG. 6A.
Figure 7A:
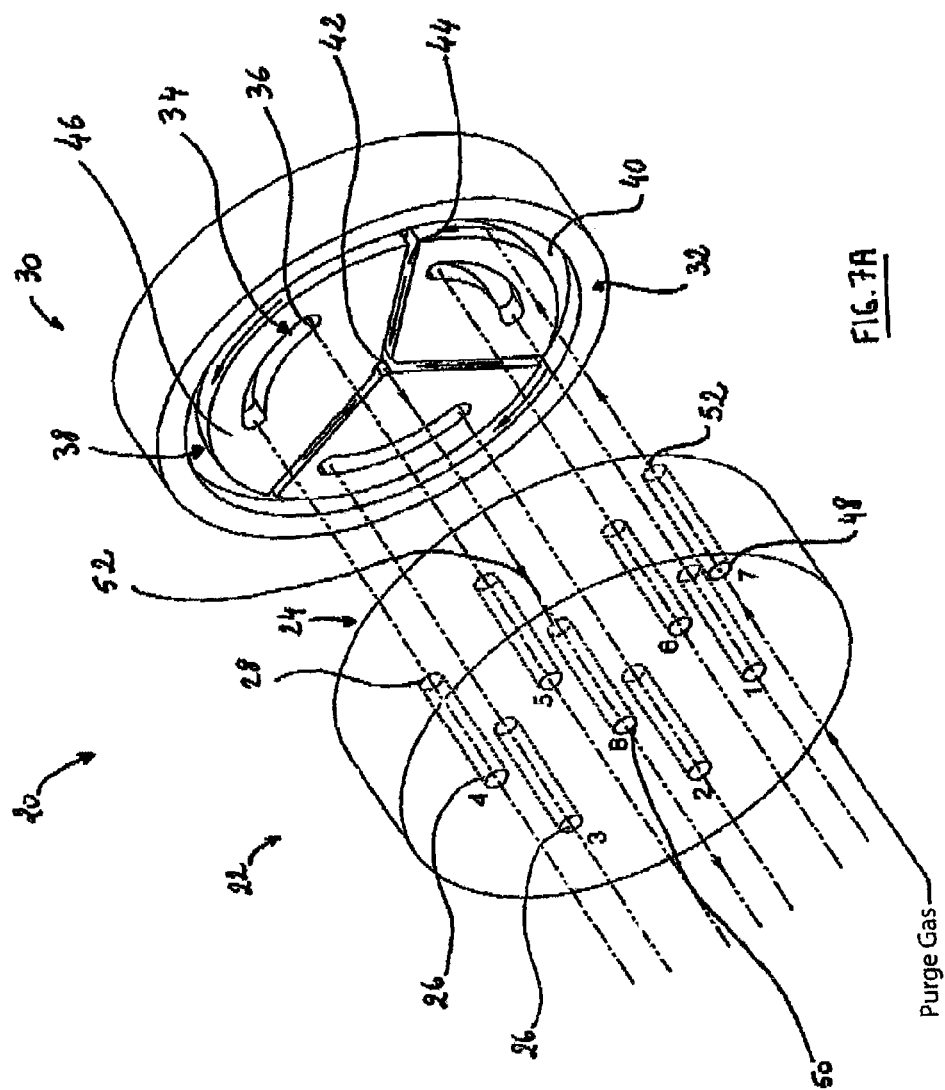
FIG. 7A is an exploded perspective view of a rotary valve according to a preferred embodiment of the present invention.
Figure 7C:
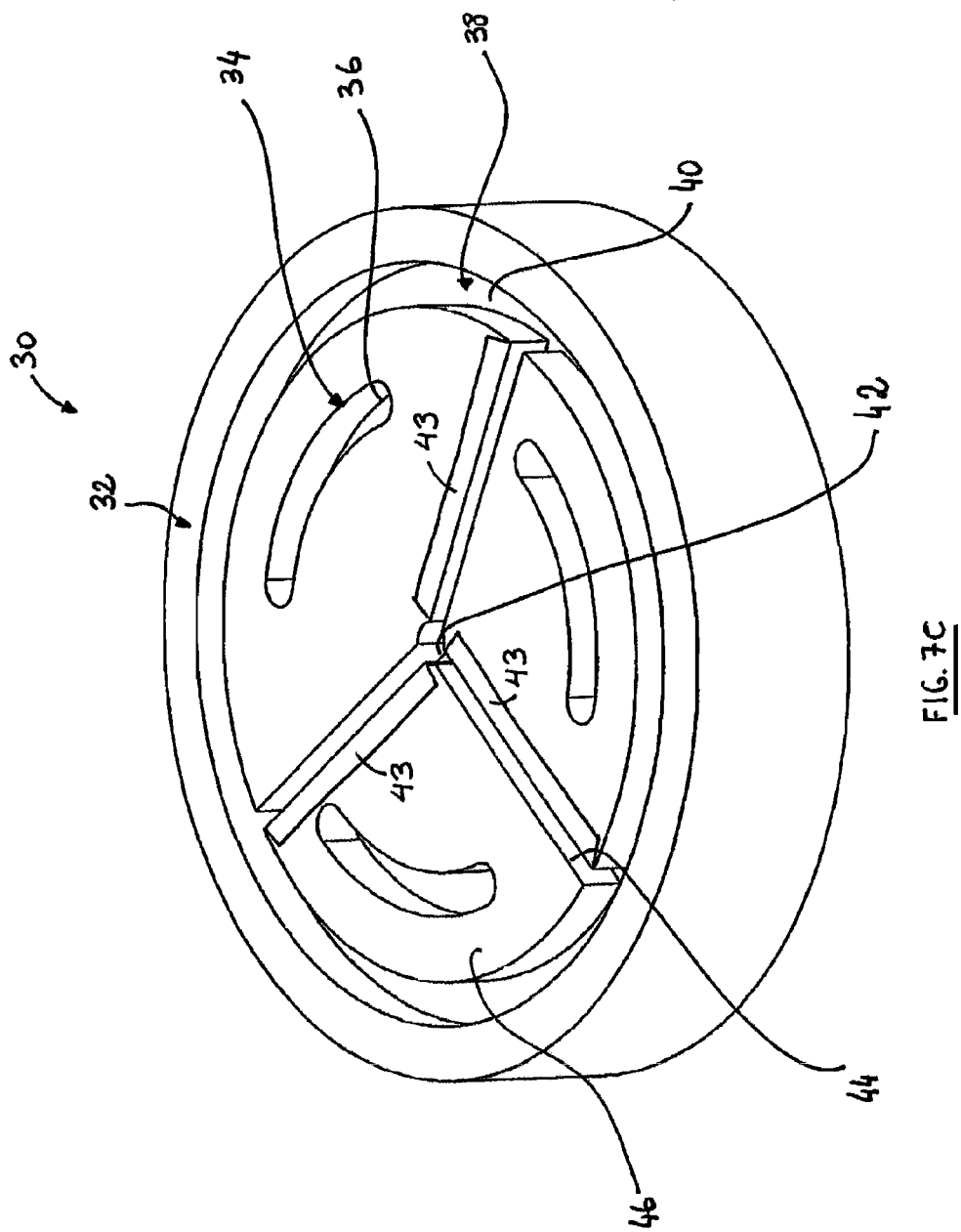
FIG. 7C is a perspective view of the rotor of the rotary valve shown in FIG. 7A.
Figure 7D:
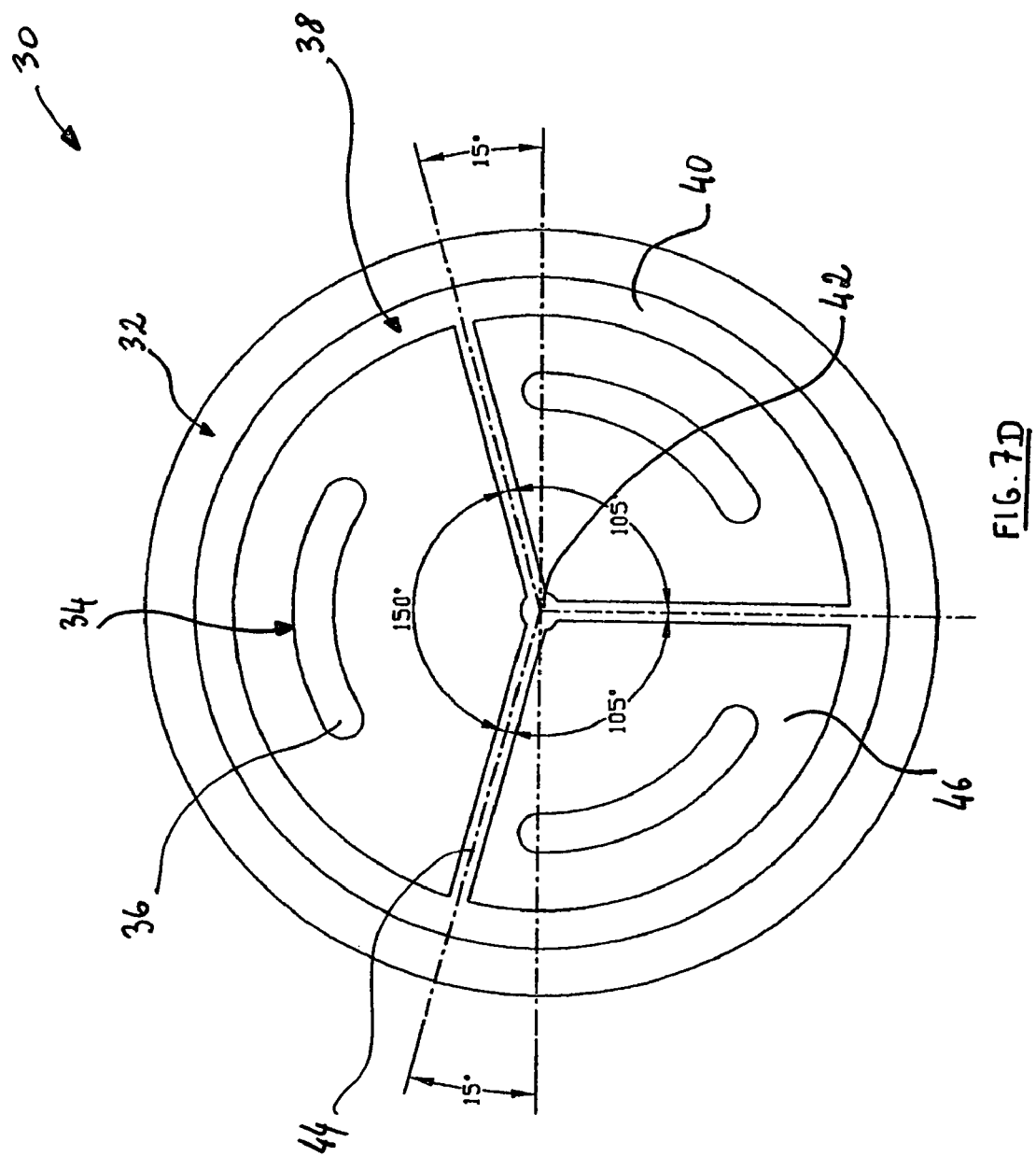
FIG. 7D is a front plan view of the rotor shown in FIG. 7C.

While the invention will be described in conjunction with example embodiments, it will be understood that it is not intended to limit the scope of the invention to such embodiments. On the contrary, it is intended to cover all alternatives, modifications and equivalents as may be included as defined by the appended claims.

DESCRIPTION OF PREFERRED EMBODIMENTS

In the following description, similar features in the drawings have been given similar reference numerals and in order to weight down the figures, some elements are not referred to in some figures if they were already identified in a precedent figure.

The present invention relates to a rotary valve for injecting sample fluid into a flowing fluid or to individually select process fluids from a plurality of process sample points. It could also be used for multi-function fluid and flow path for gas chromatography. Thus, the present invention provides a multi-port and a multi-positions rotary valve and a method that can be used for sample stream selections, sample injection or multi-function valves used in analytical systems or in industrial application like hydraulic and pneumatic systems. It should be understood that throughout the present description, the expression "fluid" is intended to cover any fluid such as gas or liquid. In other words, the rotary valve of the present invention is intended to be used in gas analytical system or in liquid analytical systems.

The present invention alleviates the most glaring problems of the prior art in providing an improved rotary valve having the following characteristics: there are no dead volumes nor cross-port leaks. The valve is inert in that there is no adsorption nor out-gassing. The rotary valve is operable under vacuum up to many thousand psi. The rotary valve is also operable at high temperatures and prevents inboard and outboard leaks. The rotary valve advantageously has a self cleaning action. The rotary valve has a long lifetime, i.e. three years and more, even in continuous use. Moreover, the present rotary valve does not rely on elastomer or O-ring type seals in the critical fluid flow path. Furthermore, the present rotary valve can advantageously be used in an analytical chromotographic system which is self-diagnostic, so end of life of the valve could be determined in real time. Besides, the present invention provides an alternative method that can be used to retrofit existing designs and makes them last longer with the pre-cited characteristics.

The heart of the method is based on the addition of extra recesses in the rotor and extra ports in the stator. These recesses allow to cancel the effect of any possible leaks by evacuating them. They also evacuate particles build up. Preferably, the materials used for the manufacturing of the rotor and stator provide a good inertness and high temperature capability. The shape of the recess edge and material used for rotor and stator advantageously provide the long mechanical life.

Referring to FIGS. 7A to 7D, there is shown a six-port rotary valve 20 using the concept that makes the object of the present invention. The rotary valve 20 comprises a stator 22 having a stator interface 24 and a plurality of fluid open-ports 26. Each of the ports 26 has an opening 28 lying at the stator interface 24. The rotary valve is also provided with a rotor 30 coaxial to the stator 22 and rotatable about an axis with respect to the stator 22 between each of a plurality of rotor positions. The rotor 30 has a rotor interface 32 lying against the stator interface 24 and at least one fluid channel 34 provided with an opening 36 extending in the rotor interface 32 for operatively interacting with the fluid open-ports 26 of the stator 22. In the illustrated embodiment, each of the stator interface 24 and rotor interface 32 has a planar shape. However, these interfaces could also be conically or spherically shaped. These interfaces could also have any convenient shape as known in the art.

The rotary valve 20 is also provided with a fluid circulation line having a looped recessed fluid circuit 38 extending in the rotor interface 32. The looped fluid circuit 38 has an outer annular recess 40 and an inner recess 42, each extending in the rotor interface 32. The fluid circuit 38 further has a plurality of separation recesses 44 radially extending in the rotor interface 32. Each of the separation recesses 44 is connected to each of the inner and outer recesses 42, 40 for defining a plurality of rotor interface portions 46 isolated from each others.

Each of the rotor interface portions 46 encloses at the most one of the fluid channels 34. It is understood by this that any given rotor interface portion may enclose an entire fluid channel, a portion of such a channel or none at all. However, no part of two different channels can be found within a single rotor interface portion; in this manner, the boundaries of the rotor interface portions will provide a barrier against cross-contamination between the different channels. The fluid circulation line is also provided with a fluid inlet 48 and a fluid outlet 50, each having an opening 52 lying at the stator interface 24. Each of the inlet and outlet 48, 50 is in continuous fluid communication with a respective one of the inner and outer recesses 42, 40 for providing a continuous fluid flow in the looped recessed fluid circuit 38. As illustrated, the inner recess 42 preferably has a round shape diametrically corresponding to the opening 52 of a respective one of the fluid inlet and outlet 48, 50.

Still referring to FIGS. 7A to 7D, in the illustrated preferred embodiment, preferably, each of the three fluid channels 34 extends in a respective one of the three rotor interface portions 46. Each of the fluid channels 34 is particularly shaped for connecting two adjacent ports 26 when the rotor 30 is in one of the rotor positions, thereby providing a fluid flow path between the two adjacent ports 26 in said position. Preferably, the ports 26 are circularly arranged in a port circle concentrical with the stator interface 24 between the inner and outer recesses 42, 40 of the rotor 30. Each of the fluid channels 34 preferably curvely extends in the rotor interface 32 coincidentally with the circle. As can be seen in this illustrated embodiment, each of the fluid channels 34 preferably has its opening 36 opened lengthwise in the rotor interface 32 for precisely linking the two adjacent ports 26. However, it should be noted that each of the fluid channels 34 could also extends inside the rotor 30 and be provided with first and second openings extending in the rotor interface 32, each being aligned with the respective port 26 for linking the two adjacent ports 26.

Thus, in this preferred embodiment, the fluid open-ports 26 of the valve 20 provide a carrier gas circuit and a sample gas one connected to and passing through the valve 20, like any other conventional sample injection six-port valve system. It should be understood that any convenient number of ports 26 could also be envisaged for a specific application.

However, the continuous fluid flow in the looped recessed fluid circuit 38 provides an extra gas circuit into the valve 20. Carrier gas is introduced at the inlet 48, sweeping the outer annular recess 40 and separation recesses 44, and then exiting the valve 20 at the outlet 50. Of course, it is to be understood that the positions of the inlet 48 and the outlet 50 may be interchanged.

When the valve needs to be rotated or actuated, this is done in the same way as the other six-port rotary valves, i.e. by rotating the rotor 30 on the stator 22, as illustrated in FIGS. 8A to 8E.

The rotor 30 is rotated from the position shown in 8A to intermediate positions 8B, 8C, and 8D and ending at final position 8E. Positions 8B, 8C, and 8D show that there is only one separation recess 44 at a time that passes over any ports 26 of the stator 22. Thus, in this preferred embodiment, each of the separation recesses 44 preferably extends at a predetermined position so that at most one of the ports 26 is in fluid communication with the looped fluid circuit 38 for any relative orientation of the rotor 30 with respect to the stator 22, as can be shown in FIG. 7D. This prevents a short circuit or a connection between stator critical ports 26, which is particularly advantageous in cases where cross-contamination between different parts could lead to an explosive or otherwise dangerous reaction.

When the valve 20 is at one of its final positions, i.e. 8A or 8E, any leak from any of the three pairs of ports 26 will reach one of the separation recesses 44 and will be carried away from the valve 20 by the pure carrier sweeping gas of the circulation line. This way, the leak is evacuated from the valve 20 without interfering with the process of impurities identification and quantification or other primary function of the valve. Thus, the separation recesses 44 allow to eliminate the effect of any cross-port leak that could appear over the time because of wearing of the rotor or stator interfaces 24, 32. Moreover, the outer annular recess 40 prevents any inboard or outboard leaks from the valve 20. If it happens, the outboard and inboard leaks are evacuated out of the valve 20 and do not reach critical analytical flow path. Moreover, the outer annular recess 40 acts as an active seal. Thus, it seals and evacuates leaks at the same time.

In a further embodiment, the rotary valve is preferably provided with a sealed housing for sealably enclosing the rotor 30 and the stator 22 therein. The housing is purged by the carrier gas. Thus, it isolates completely the valve's critical analytical flow path from its environment.

Referring again to FIGS. 7A to 7D, in this preferred embodiment, the rotor 30 and the stator 22 are preferably made of ultra hard ceramic, such as for example Alumina or Zirconia. The rotor and stator interfaces 32, 24 are preferably polished so well that just the fact of putting the rotor 30 on the stator 22 evacuates ambient air between both faces and creates a vacuum. Furthermore, these interfaces 34, 32 could be coated with various materials acting as lubricants for increasing the quality of the surface. The type of coating to be used depends of which operating conditions the valves will be used in, i.e. temperature and type of fluid. These parameters are well known from people involved in the art and will not be further described therein.

Another advantageous feature of the valve 20 of the preferred embodiment of present invention is the absence of sharp edges on the border of the recesses and ports made in ceramic. Instead of a sharp edge, each of the fluid open-ports 26 of the stator 22 preferably has a down sloped edge or a round shape. The opening 36 of the fluid channel 34 also preferably has a down sloped edge or a round shape. Each of the inner recess 42, outer recess 40 and separation recesses 44 is also advantageously provided with a down sloped edge or a round shape. This eliminates the "razor blade" effect of these edges on the interfaces 24, 32 when rotor interface 32 rotates on the stator interface 24. This avoids the build-up of scratches on the interfaces that cause excessive wearing and consequently leaks. In a further preferred embodiment, each of the separation recesses 44 can advantageously be provided with a fin 43 extending on an edge thereof for increasing the mechanical sweeping effect. The fins are advantageously made of teflon but any other soft and non-absorbent material could also be envisaged. It could also be envisaged to provide a fin on each opposed edge of each of the separation recesses 44 or to provide a single fin on one of the separation recesses 44.

A factor that has limited the use of ceramic for stator in the past was the difficulty of connecting fitting tubing to it. In a preferred embodiment of the present invention, the stator has a metallic base element and a ceramic element providing the stator interface 24. The ceramic element is placed on a metallic base element to provide long life expectancy. Each of the stator elements are sealed together with the ceramic element and metallic base element having aligned passages. However, there are some drawbacks to such assembly, as described in U.S. Pat. No. 6,453,946. More particularly, there is volume added to the valve causing dispersion and the risk of leaks at high temperature. Such valves are manufactured under model #7750E-020 from Rheodyne L.P.

In our preferred embodiment of this invention, the fluid tubings are brazed to the ceramic element of the stator. This brazing is done under vacuum and provides a dead volume free and leak tight joint. The ceramic stator tubing assemblies are mounted to the base of the valve housing by passing the tubing to their corresponding ports in the valve base until the ceramic element comes seated on the plane surface of the valve base. Preferably, the stator 22 is also provided with a set of holding pins, three for example, having tight tolerances. These pins allow to maintain and align the ceramic element on the valve base. The holding pins prevent any rotation of the stator 22 due to the rotating movement of the rotor 30 and maintain a precise alignment of the stator ports 26 relative to the rotor's channels 34.

In a further preferred embodiment, the rotary valve is also provided with an actuation mechanism operatively connected to the rotor 30 for actuating the rotor in a desired one of the rotor positions. The rotor 30 is then attached to the actuation mechanism and aligned with the stator 22 at the proper and precise angle. Each of the fluid channels 34 preferably links precisely two of the stator ports 26. The valve cover and the metal gasket at its base are mounted on the valve base and properly tightened. The rotor shaft extends the valve cover. Any length of actuation shaft could be fitted in the case that the valve is installed in an oven. This way the actuation mechanism could be at ambient temperature. Actuation mechanism could be an electrical motor, solenoid, pneumatic, or simply a handle turned by hand.

Thus, with reference to FIGS. 7A to 7D, in one of the most preferred embodiment of the present invention, the rotor 30 and the stator 22 are advantageously made of ultra-hard material, i.e. ceramic (Alumina or Zirconia). The rotor and stator recesses and ports preferably have a smooth round edge instead of a sharp edge. The rotor and stator interfaces 32, 24 are advantageously highly polished and have a lubricant coating compatible with the application. The stator tubings are preferably brazed thereon. The stator 22 and the rotor 30 are advantageously mounted in a sealed housing and purged by the carrier gas. The separation recesses 44 are done at proper angle from each other in order to have only one separation recess 44 passing over a stator port 26 at a time. Such a valve is advantageously used in a chromatographic system. In this system, the carrier gas and sample gas are connected in a conventional way. There is a carrier gas connected to the inlet 48 aligned with the outer annular recess 40. This carrier gas sweeps the outer annular recess 40 and the separation recesses 44, and then exits at the stator's fluid outlet 50. Moreover, the valve 20 is advantageously provided with the sealed housing purged by the carrier gas. With these characteristics, an extremely high performance valve is obtained. Such a valve is inert, dead volume free, and unaffected by leak developed over a long period of time. The lifetime of this valve becomes very long in comparison with the valves known in the art.

Figure 11:
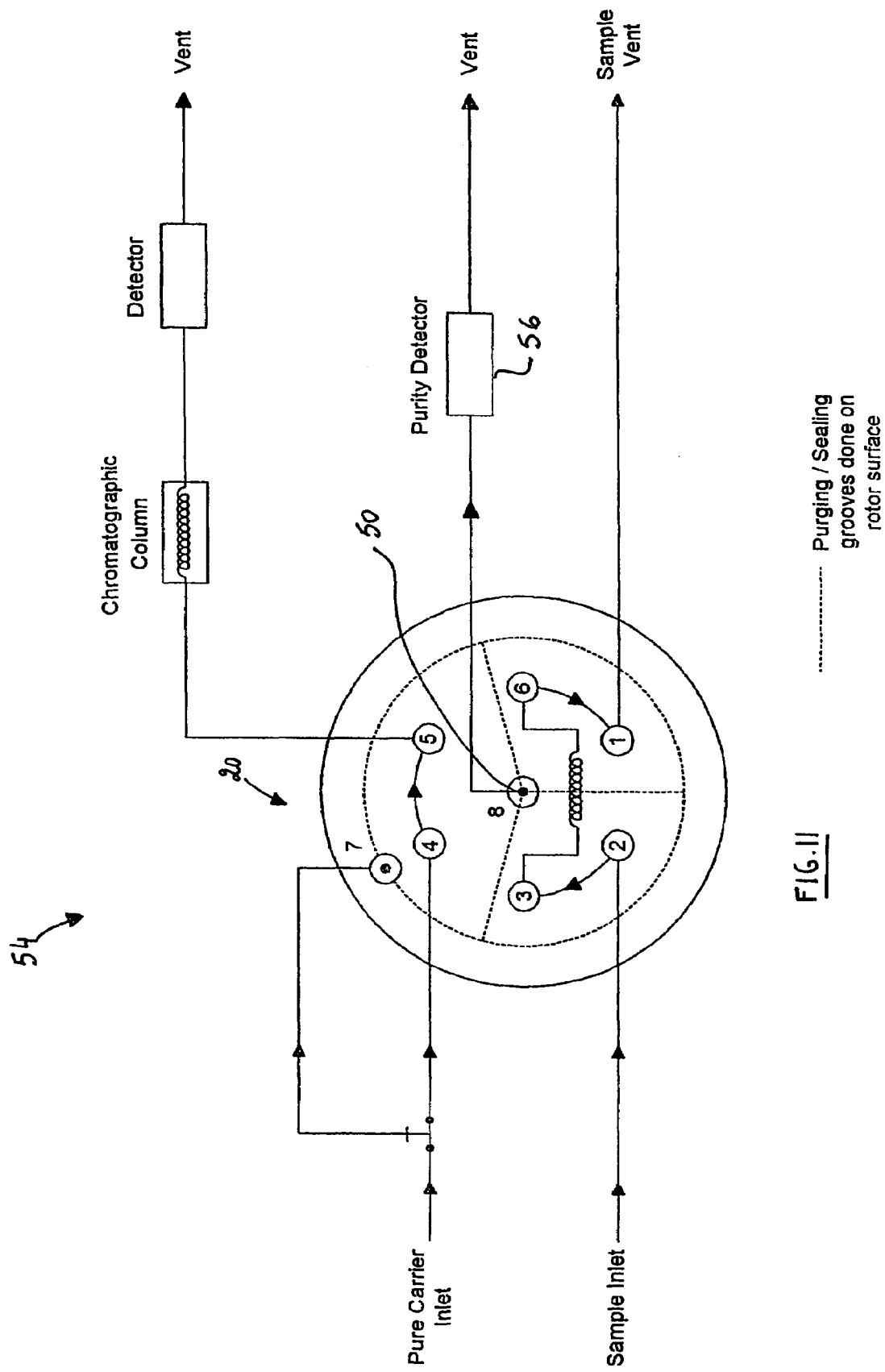
FIG. 11 is a schematic representation of a sample injection system, according to a preferred embodiment of the present invention.

Furthermore, with reference to FIG. 11, the present invention also provides an analytical chromatographic system 54 using the rotary valve 20 previously described. Such an analytical system 54 is provided with monitoring means operatively connected to the fluid outlet 50 for monitoring a fluid passing therethrough. Preferably, the monitoring means comprises a purity detector 56 for detecting contamination of said fluid. Thus, preferably, the fluid outlet 50 of the stator 22 is connected to the purity detector 56. This results in a valve diagnostic system that can warn the user when critical leaks will develop over the time due to the inevitable wearing of the elements. Any leak will change the purity of the gas flowing in the purity detector 56, the level of change in the fluid purity gives an indication of wearing and user can then take appropriate action. This is unachieved before and incredibly valuable for process chromatograph where downtime is costly. Now, with such system, maintenance can be done only when required. From tests in laboratory, such valve systems demonstrate its capability to operate for more than three years, with a gas chromatograph having Helium as a carrier gas and with a sample injection every three minutes. System performance was monitored by watching the analytical detector and the purity detector 56 mounted on the fluid outlet 50.

Even during accelerated lifetime tests done by continuously activating the valve, no inboard contamination was recorded and no analytical performance degradation was noted. And this, even if the purity detector 56 was beginning to detect some internal leak, has for effect the substantial extension of the useful lifetime of the system. Preferably, the purity detector 56 is reading in a synchronised manner, i.e. there is some delay before the actuation to avoid to read the normal "sample pulse" when one separation recess 44 passes over the sample port 26. It also appears that the separation recesses 44 not only eliminate the effect of internal leaks, and this at various operating pressures, but also have a kind of cleaning effect. The gas purge through the inner and outer recesses 42, 40 and through the separation recesses 44 carries away any particle coming from sample contamination or from interface wearing. Thus, with the above-mentioned characteristics, a chromatographic valve is no more a simple mechanical part that plagues system performance and that must be replaced frequently to avoid analytical system degradation. On the contrary, it becomes an intelligent part of the system when coupled with the purity detector. This is an advantageous feature of the present invention since the system can become self diagnostic, which is a great advantage for various process analytical equipment.

The concept of the present invention can also be very useful in other valve's port arrangements for other applications. For example, an important function in analytical systems is to measure some impurities in various sample streams. So it is required to sequentially select those various sample streams. A sample stream selector valve is then required.

Figure 9A:
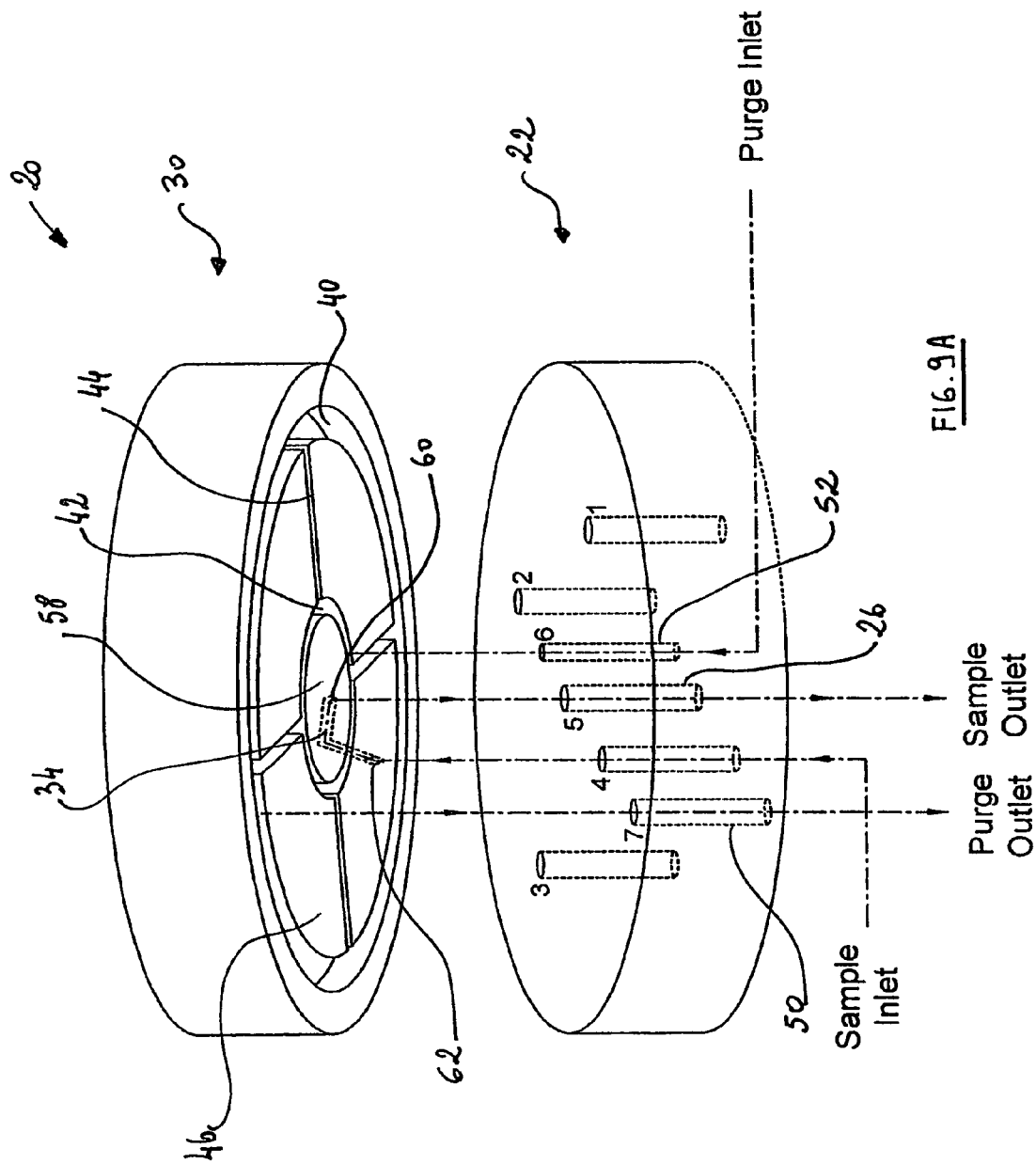
FIG. 9A is an exploded perspective view of another rotary valve, according to another preferred embodiment of the present invention.
Figure 9B:
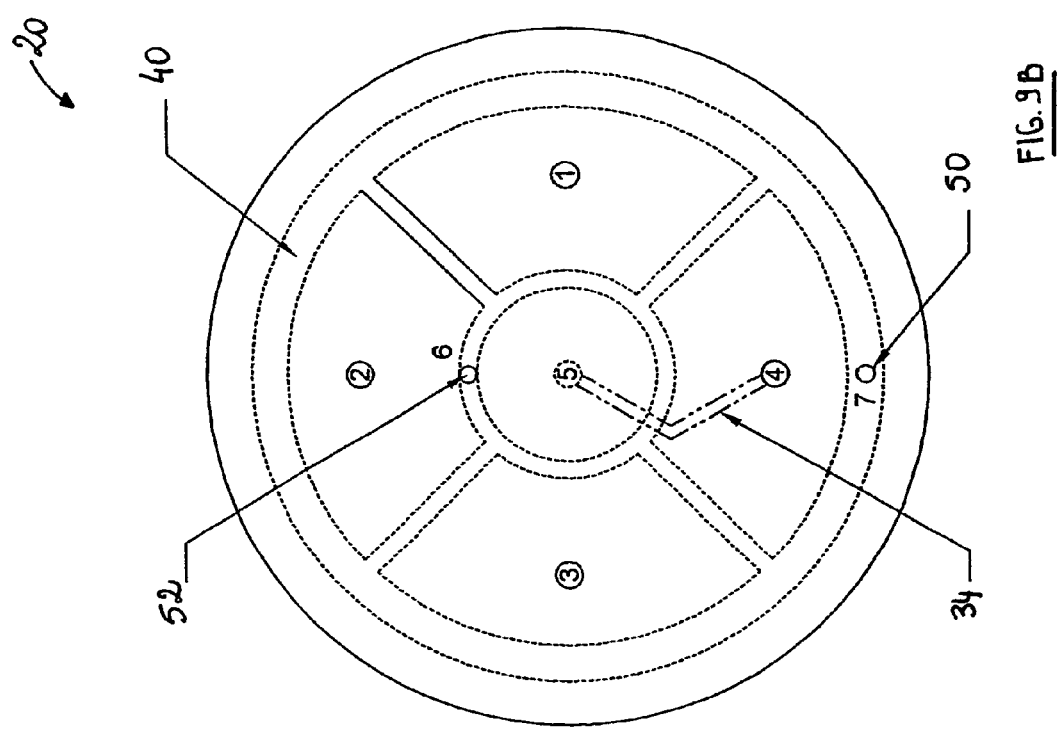
FIG. 9B is a front plan view of the rotary valve shown in FIG. 9A.

FIGS. 9A and 9B show a first preferred embodiment of the valve 20 of the present invention used in such application. This embodiment illustrates a four sample streams selection valve, but it should be understand that it is not limited to four and that it could be extended to more sample channels. In this preferred embodiment, the inner recess 42 has an annular portion defining a central rotor interface portion 58 therein. The ports 26 are particularly arranged so that at anyone of the rotor positions, one of the ports 26 is aligned with one of the rotor interface portions 46, 58. The fluid channel 34 is provided with first and second openings 60, 62 extending in the rotor interface 32. The first opening 60 extends in the central rotor interface portion 58 and provides a continuous fluid communication with a corresponding port 26 aligned therewith. The second opening 62 extends in one of the remaining rotor interface portions 46 and provides a fluid communication with a corresponding port 26 aligned therewith for a given rotor position, thereby providing a fluid flow path between the two ports 26 in simultaneous fluid communication with the first and second openings 60, 62. As illustrated, the ports 26 aligned with the remaining rotor interface portions 44 are preferably circularly arranged on a port circle concentrical with the rotor interface 32 between the inner and outer recesses 42, 40 of the rotor 30. This valve 20 can also advantageously be mounted in a purge housing, similarly to the injection valve previously described. These characteristics provide a dead volume free and cross-ports leak free sample stream selection valve. Again, the lifetime of this valve is by far longer then any rotary sample stream selection valve known in the art. The sample stream is selected by turning the rotor 30 over the stator 22. The inner and outer recesses 42, 40 and the separation recesses 44 are purged with a clean and high purity gas. This purging could be at positive pressure or under vacuum. The object of this purging is again to evacuate any leak that may contaminate the selected sample outside the valve 20. Inboard and outboard contaminations are eliminated by the outer annular recess 40 and the purge housing enclosing the valve.

As in a previously described preferred embodiment and with reference to FIG. 11, it is also possible to provide an analytical system which is self diagnostic by monitoring the purity of the purge gas exiting the valve at the fluid outlet 50. In applications highly critical like in explosive detection or toxic gas, the valve 20 shown in FIGS. 9A and 9B is of high value since user can be sure of the system integrity. The sample is not contaminated by the sample stream selection system.

Still with reference to FIG. 11, it should also be understood that, for a particular application, a plurality of valves of the present invention could also be combined in an analytical system. Each of the valves could be provided with its own purity detector 56. However, in using an additional sample streams selection valve connected to each of the other valves, a single purity detector 56 connected to the sample steams selection valve could be used for monitoring the fluid passing through each of the valves. This particular arrangement would allow to detect contamination of each of the fluids without dramatically increasing the cost of the system.

Figure 10:
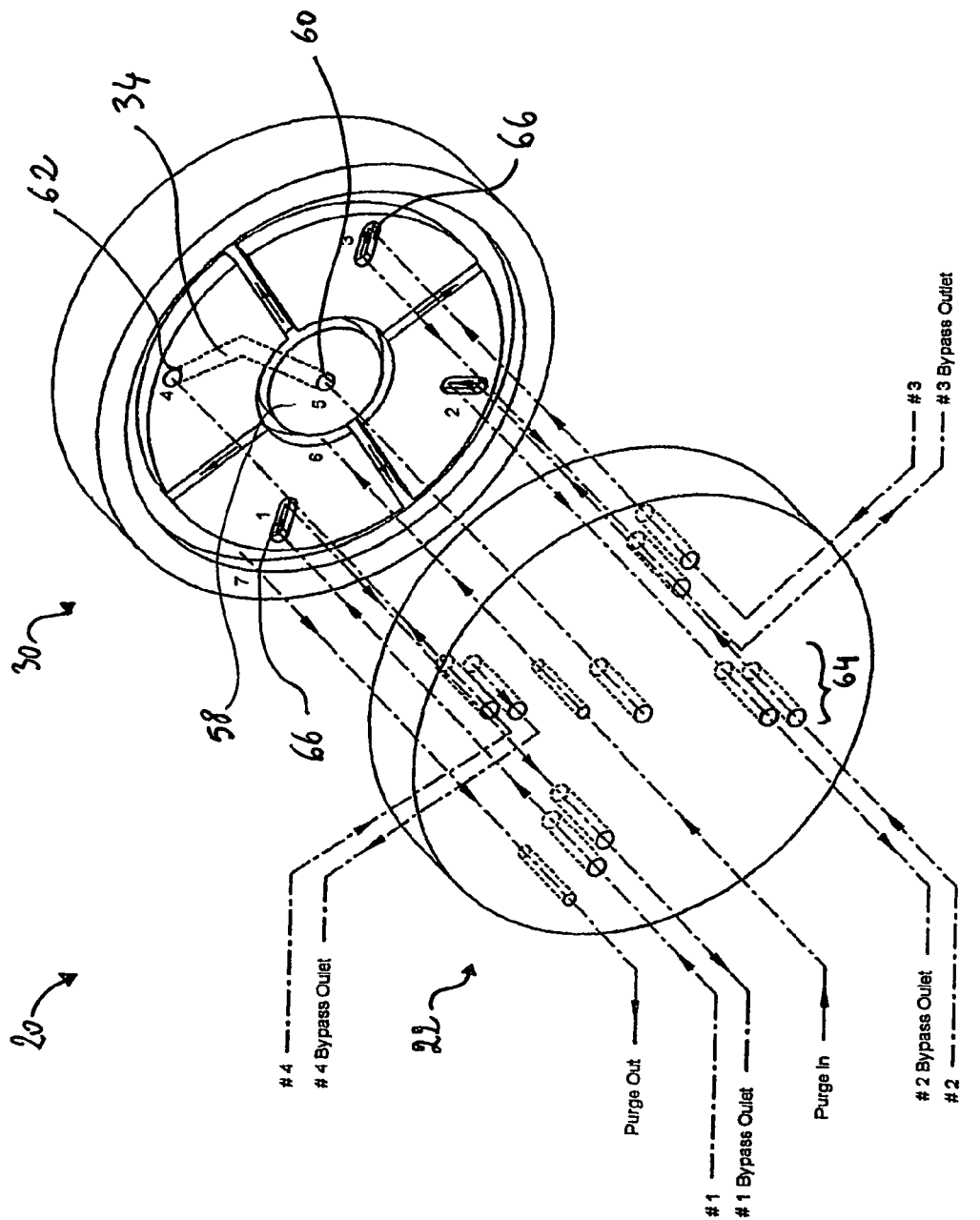
FIG. 10 is an exploded perspective view of another rotary valve, according to another preferred embodiment of the present invention.

Another advantageous variation of a sample stream selection based on this method is illustrated in FIG. 10. In this case, the unselected samples are by-passed to keep a constant flow and are individually vented outside the system. This is very useful when the various samples are not the same type and then, not compatible. In the illustrated embodiment, one of the ports 26 is aligned with the central rotor interface portion 58. The remaining ports 26 are preferably arranged in pairs 64 of first and second ports. Each of the pairs 64 is aligned with one of the rotor interface portions 46 for a given position. The fluid channel 34 has first and second openings 60, 62 extending in the rotor interface 32. The first opening 60 extends in the central rotor interface portion 58 and provides a continuous fluid communication with the corresponding port 26 aligned therewith. The second opening 62 extends in one of the remaining rotor interface portions 46 and provides a fluid communication with one port 26 of a corresponding pair 64 aligned therewith for a given rotor position, thereby providing a fluid flow path between the two ports 26 in simultaneous fluid communication with the first and second openings 60,

62. The rotor 30 is further advantageously provided with a plurality of recessed grooves 66, each of the recessed grooves 66 extending in a respective one of the remaining rotor interface portions 46 for respectively connecting each port 26 of a corresponding pair 64 together in one of the rotor positions, thereby providing a vent fluid flow path between each port 26 of the corresponding pair 64. As illustrated, each first port of each of the pairs 64 is preferably circularly arranged on a first port circle concentrical with the rotor interface 32. Each second port of each of the pairs 64 is preferably circularly arranged on a second circle concentrical with the rotor interface 32. Of course, any other convenient arrangement of the ports 26 could also be envisaged according to a particular application.

FIGS. 12A and 12B illustrate another preferred embodiment of the present invention. This embodiment shows a conical valve like the ones made by Valco Company, but manufactured according to the concept of the present invention. This valve 20 has also been tested in laboratory and has demonstrated an excellent performance with Helium as carrier gas. Lifetime expectancy has been proven to be at least three times longer than with the unmodified version. This is a real improvement for many systems installed in the field.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A rotary valve comprising:
   a stator having a stator interface and a plurality of fluid open-ports, each of said ports having an opening lying at said stator interface;
   a rotor coaxial to said stator and rotatable about an axis with respect to said stator between each of a plurality of rotor positions, said rotor having a rotor interface lying against said stator interface and at least one fluid channel provided with an opening extending in said rotor interface for operatively interacting with the fluid open-ports of the stator; and
   a fluid circulation line comprising:
   a looped recessed fluid circuit extending in said rotor interface, said looped fluid circuit comprising an outer annular recess and an inner recess, each extending in said rotor interface, said fluid circuit further comprising a plurality of separation recesses radially extending in said rotor interface, each of said separation recesses being connected to each of said inner and outer recesses for defining a plurality of rotor interface portions isolated from each others, each of said rotor interface portions enclosing at the most one of the fluid channels, said plurality of separation recesses extending at a predetermined position so that at most one of said ports is in fluid communication with said looped fluid circuit for any relative orientation of the rotor with respect to the stator; and
   a fluid inlet and a fluid outlet, each having an opening lying at said stator interface, each of said inlet and outlet being in continuous fluid communication with a respective one of said inner and outer recesses for providing a continuous fluid flow in said looped recessed fluid circuit.

2. The rotary valve according to claim 1, wherein each of said fluid channels extends in a respective one of said rotor interface portions, each of said fluid channels being particularly shaped for connecting two adjacent ports when said rotor is in one of said rotor positions, thereby providing a fluid flow path between said two adjacent ports in said position.

3. The rotary valve according to claim 2, wherein said ports are circularly arranged in a port circle concentrical with said stator interface between said inner and outer recesses of said rotor, each of said fluid channels curvely extending in said rotor interface coincidentally with said circle.

4. The rotary valve according to claim 1, wherein said inner recess has a round shape diametrically corresponding to the opening of a respective one of said fluid inlet and outlet.

5. The rotary valve according to claim 1, wherein said inner recess comprises an annular portion defining a central rotor interface portion therein.

6. The rotary valve according to claim 5, wherein said fluid channel comprises first and second openings extending in said rotor interface, the first opening extending in said central rotor interface portion and providing a continuous fluid communication with a corresponding port aligned therewith, the second opening extending in one of the remaining rotor interface portions and providing a fluid communication with a corresponding port aligned therewith for a given rotor position, thereby providing a fluid flow path between the two ports in simultaneous fluid communication with said first and second openings.

7. The rotary valve according to claim 6, wherein said ports aligned with said remaining rotor interface portions are circularly arranged on a port circle concentrical with said rotor interface between said inner and outer recesses of said rotor.

8. The rotary valve according to claim 5, wherein one of said ports is aligned with said central rotor interface portion, the remaining ports being arranged in pairs of first and second ports, each of said pairs being aligned with one of said rotor interface portions for a given position, said fluid channel comprising first and second openings extending in said rotor interface, the first opening extending in said central rotor interface portion and providing a continuous fluid communication with the corresponding port aligned therewith, the second opening extending in one of the remaining rotor interface portions and providing a fluid communication with one port of a corresponding pair aligned therewith for a given rotor position, thereby providing a fluid flow path between the two ports in simultaneous fluid communication with said first and second openings, said rotor further comprising a plurality of recessed grooves, each of said recessed grooves extending in a respective one of said remaining rotor interface portions for respectively connecting each port of a corresponding pair together in one of said rotor positions, thereby providing a vent fluid flow path between each port of the corresponding pair.

9. The rotary valve according to claim 8, wherein each first port of each of said pairs is circularly arranged on a first port circle concentrical with said rotor interface, each second port of each of said pairs being circularly arranged on a second circle concentrical with said rotor interface.

10. The rotary valve according to claim 1, wherein each of said stator interface and rotor interface has a planar shape.

11. The rotary valve according to claim 1, wherein each of said stator interface and rotor interface has a conical shape.

12. The rotary valve according to claim 1, wherein the opening of each of said fluid open-ports has a smooth sloped edge.

13. The rotary valve according to claim 1, wherein the opening of said fluid channel has a smooth sloped edge.

14. The rotary valve according to claim 1, wherein each of said inner recess, outer recess and separation recesses has a smooth sloped edge.

15. The rotary valve according to claim 1, wherein each of the stator and the rotor is made of ultra hard ceramic.

16. The rotary valve according to claim 1, wherein each of the stator interface and the rotor interface is polished.

17. The rotary valve according to claim 1, wherein each of the stator interface and the rotor interface has a coating.

18. The rotary valve according to claim 1, wherein said rotary valve further comprises at least one fin, each of said fins extending on an edge of one of the separation recesses.

19. An analytical chromatographic system comprising:
a rotary valve as defined in claim 1; and
monitoring means operatively connected to the fluid outlet for monitoring a fluid passing therethrough.

20. The analytical chromatographic system according to claim 19, wherein said monitoring means comprises a purity detector for detecting contamination of said fluid.

21. The analytical chromatographic system according to claim 19, wherein said monitoring means synchronically monitors said fluid.

22. A rotary valve comprising:
A stator having a stator interface and a plurality of fluid open-ports, each of said ports having an opening lying at said stator interface;
a rotor coaxial to said stator and rotatable about an axis with respect to said stator between each of a plurality of rotor positions, said rotor having a rotor interface lying against said stator interface and at least one fluid channel provided with an opening extending in said rotor interface for operatively interacting with the fluid open-ports of the stator; and
a fluid circulation line comprising:
a looped recessed fluid circuit extending in said rotor interface, said looped fluid circuit comprising an outer annular recess and an inner recess, each extending in said rotor interface, said inner recess comprising an annular portion defining a central rotor interface portion therein, said fluid circuit further comprising a plurality of separation recesses radially extending in said rotor interface, each of said separation recesses being connected to each of said inner and outer recesses for defining a plurality of rotor interface portions isolated from each others, each of said rotor interface portions enclosing at the most one of the fluid channels, said fluid channel comprising first and second openings extending in said rotor interface, the first opening extending in said central rotor interface portion and providing a continuous fluid communication with a corresponding port aligned therewith, the second opening extending in one of the remaining rotor interface portions and providing a fluid communication with a corresponding port aligned therewith for a given rotor position, thereby providing a fluid flow path between the two ports in simultaneous fluid communication with said first and second openings; and
a fluid inlet and a fluid outlet, each having an opening lying at said stator interface, each of said inlet and outlet being in continuous fluid communication with a respective one of said inner and outer recesses for providing a continuous fluid flow in said looped recessed fluid circuit.

23. The rotary valve according to claim 22, wherein said ports aligned with said remaining rotor interface portions are circularly arranged on a port circle concentrical with said rotor interface between said inner and outer recesses of said rotor.

24. The rotary valve according to claim 22, wherein one of said ports is aligned with said central rotor interface portion, the remaining ports being arranged in pairs of first and second ports, each of said pairs being aligned with one of said rotor interface portions for a given position, said fluid channel comprising first and second openings extending in said rotor interface, the first opening extending in said central rotor interface portion and providing a continuous fluid communication with the corresponding port aligned therewith, the second opening extending in one of the remaining rotor interface portions and providing a fluid communication with one port of a corresponding pair aligned therewith for a given rotor position, thereby providing a fluid flow path between the two ports in simultaneous fluid communication with said first and second openings, said rotor further comprising a plurality of recessed grooves, each of said recessed grooves extending in a respective one of said remaining rotor interface portions for respectively connecting each port of a corresponding pair together in one of said rotor positions, thereby providing a vent fluid flow path between each port of the corresponding pair.

25. the rotary valve according to claim 22, wherein each first port of each of said pairs is circularly arranged on a first port circle concentrical with said rotor interface, each second port of each of said pairs being circularly arranged on a second circle concentrical with said rotor interface.

26. A rotary valve comprising:
a stator having a stator interface and a plurality of fluid open-ports, each of said ports having an opening lying at said stator interface;
a rotor coaxial to said stator and rotatable about an axis with respect to said stator between each of a plurality of rotor positions, said rotor having a rotor interface lying against said stator interface and at least one fluid channel provided with an opening extending in said rotor interface for operatively interacting with the fluid open-ports of the stator; and
a fluid circulation line comprising:
a looped recessed fluid circuit extending in said rotor interface, said looped fluid circuit comprising an outer annular recess and an inner recess, each extending in said rotor interface, said fluid circuit further comprising a plurality of separation recesses radially extending in said rotor interface, each of said separation recesses being connected to each of said inner and outer recesses for defining a plurality of rotor interface portions isolated from each others, each of said rotor interface portions enclosing at the most one of the fluid channels; and
a fluid inlet and a fluid outlet, each having an opening lying at said stator interface, each of said inlet and outlet being in continuous fluid communication with a respective one of said inner and outer recesses for providing a continuous fluid flow in said looped recessed fluid circuit wherein said rotary valve further comprises at least one fin, each of said fins extending on an edge of one of the separation recesses.

* * * * *